(12) United States Patent
Madrid et al.

(10) Patent No.: US 9,382,523 B2
(45) Date of Patent: *Jul. 5, 2016

(54) METHOD OF PRODUCING A LIPOLYTIC ENZYME

(71) Applicant: Dupont Nutrition Biosciences APS, Copenhagen K (DK)

(72) Inventors: Susan Madrid, Millbrae, CA (US); Cherry Lin, Sunnyvale, CA (US); Masoud Rajabi Zargahi, Aarhus N. (DK); Rikke Høegh Lorentsen, Brabrand (DK); Mai Faurschou Isaksen, Brabrand (DK); Michael Ward, San Francisco, CA (US)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,016

(22) Filed: Nov. 7, 2014

(65) Prior Publication Data

US 2015/0064309 A1 Mar. 5, 2015

Related U.S. Application Data

(63) Continuation of application No. 13/265,712, filed as application No. PCT/IB2010/051802 on Apr. 23, 2010, now Pat. No. 8,940,519.

(60) Provisional application No. 61/172,272, filed on Apr. 24, 2009.

(30) Foreign Application Priority Data

May 20, 2009 (GB) .................................... 0908770.1

(51) Int. Cl.
*C12N 15/80* (2006.01)
*C12N 9/20* (2006.01)
*A23K 1/165* (2006.01)
*A23L 1/03* (2006.01)
*A23L 1/30* (2006.01)

(52) U.S. Cl.
CPC ................ *C12N 9/20* (2013.01); *A23K 1/1653* (2013.01); *A23L 1/034* (2013.01); *A23L 1/3016* (2013.01); *C12N 15/80* (2013.01); *A23V 2002/00* (2013.01); *C12Y 301/01003* (2013.01)

(58) Field of Classification Search
CPC ................................ A23K 1/1653; C12N 9/20
USPC .................... 435/198, 252.3, 320.1; 536/23.2
See application file for complete search history.

(56) References Cited

U.S. PATENT DOCUMENTS

| | | | | |
|---|---|---|---|---|
| 6,638,737 B1 * | 10/2003 | Derkx | .............. | C12N 9/20 435/233 |
| 6,852,346 B2 * | 2/2005 | Søe | .............. | A21D 2/16 426/18 |
| 8,940,519 B2 * | 1/2015 | Madrid | .............. | A23K 1/1653 435/198 |

* cited by examiner

*Primary Examiner* — Tekchand Saidha

(57) ABSTRACT

The present invention provides a transformed or transfected *Trichoderma reesei* cell comprising one or more of: (i) at least one heterologous nucleotide sequence encoding a lipolytic enzyme comprising an amino acid sequence shown as SEQ ID NO: 1 or SEQ ID NO: 2, (ii) at least one heterologous nucleotide sequence encoding a lipolytic enzyme wherein the nucleotide sequence comprises the nucleotide sequence shown as SEQ ID NO: 3 or SEQ ID NO: 4, or (iii) at least one heterologous nucleotide sequence encoding a lipolytic enzyme wherein the nucleotide sequence comprises the nucleotide sequence which hybridizes to SEQ ID NO: 3 or SEQ ID NO: 4 or a nucleotide sequence which is at least 40% sequence identity to SEQ ID NO: 3 or SEQ ID NO: 4; and culturing the cell under conditions to allow for expression of the heterologous nucleotide sequence(s) encoding the lipolytic enzyme.

18 Claims, 17 Drawing Sheets

```
        10         20         30         40         50         60
SVSTSTLDEL QLFAQWSAAA YCSNNIDSKD SNLICTANAC PSVEEASTTM LLEFDLTNDF
        70         80         90        100        110        120
GGTAGFLAAD NTNKRLVVAF RGSSTIENWI ANLDFILEDN DDLCTGCKVH TGFWKAWESA
       130        140        150        160        170        180
ADELTSKIKS AMSTYSGYTL YFTGHSLGGA LATLGATVLR NDGYSVELYT YGCPRIGNYA
       190        200        210        220        230        240
LAEHITSQGS GANFRVTHLN DIVPRVPPMD FGFSQPSPEY WITSGNGASV TASDIEVIEG
       250        260        270
INSTAGNAGE ATVSVVAHLW YFFAISECLL
```

FIG. 1.

| EXPRESSION HOST | LIPASE 3 % YIELD INCREASE |
|---|---|
| 1. ASPERGILLUS TUBIGENSIS | 100 |
| 2. PICHIA PASTORIS | 570 |
| 3. HANSENULA POLYMORPHA | 850 |
| 4. TRICHODERMA REESEI | 4200 |
| 5. TRICHODERMA REESEI | 8570 |

*FIG. 8.*

SEQUENCE ID #1

```
  1  MFSGRFGVLL TALAALGAAA PAPLAVRSVS TSTLDELQLF AQWSAAAYCS
 51  NNIDSKDSNL TCTANACPSV EEASTTMLLE FDLTNDFGGT AGFLAADNTN
101  KRLVVAFRGS STIENWIANL DEILEDNDDL CTGCKVHTGF WKAWESAADE
151  LTSKIKSAMS TYSGYTLYFT GHSLGGALAT LGATVLRNDG YSVELYTYGC
201  PRIGNYALAE HITSQGSGAN FRVTHLNDIV PRVPPMDFGF SQPSPEYWIT
251  SGNGASVTAS DIEVIEGINS TAGNAGEATV SVVAHLWYFF AISECLL
```

LIPASE 3 AMINO ACID SEQUENCE WITH SIGNAL PEPTIDE (IN BOLD)

*FIG. 15.*

SEQ. ID # 2

| | |
|---|---|
| 1 | SVSTSTLDEL QLFAQWSAAA YCSNNIDSKD SNLTCTANAC PSVEEASTTM |
| 51 | LLEFDLTNDF GGTAGFLAAD NTNKRLVVAF RGSSTIENWI ANLDFILEDN |
| 101 | DDLCTGCKVH TGFWKAWESA ADELTSKIKS AMSTYSGYTL YFTGHSLGGA |
| 151 | LATLGATVLR NDGYSVELYT YGCPRIGNYA LAEHITSQGS GANFRVTHLN |
| 201 | DIVPRVPPMD FGFSQPSPEY WITSGNGASV TASDIEVIEG INSTAGNAGE |
| 251 | ATVSVVAHLW YFFAISECLL |

LIPASE 3 AMINO ACID SEQUENCE (WITHOUT SIGNAL PEPTIDE)

*FIG. 16.*

SEQ. ID #3 WITH SIGNAL SEQ

**ATGTTCTCTGGACGGTTTGGAGTGCTTTTGACAGCGCTTGCTGCGCTGGGTGC
TGCCGCGCCGGCACCGCTTGCTGTGCGG**Agtaggtgtgcccgatgtgagatggttggatagcact
gatgaagggtgaatagGTGTCTCGACTTCCACGTTGGATGAGTTGCAATTGTTCGCGCA
ATGGTCTGCCGCAGCTTATTGCTCGAATAATATCGACTCGAAAGACTCCAACTTG
ACATGCACGGCCAACGCCTGTCCATCAGTCGAGGAGGCCAGTACCACGATGCT
GCTGGAGTTCGACCTgtatgtcactcagatcgcagacatagagcacagctaatttgaacagGACGAAC
GACTTTGGAGGCACAGCCGGTTTCCTGGCCGCGGACAACACCAACAAGCGGCT
CGTGGTCGCCTTCCGGGGAAGCAGCACGATTGAGAACTGGATTGCTAATCTTGA
CTTCATCCTGGAAGATAACGACGACCTCTGCACCGGCTGCAAGGTCCATACTGG
TTTCTGGAAGGCATGGGAGTCCGCTGCCGACGAACTGACGAGCAAGATCAAGT
CTGCGATGAGCACGTATTCGGGCTATACCCTATACTTCACCGGGCACAGTTTGG
GCGGCGCATTGGCTACGCTGGGAGCGACAGTTCTGCGAAATGACGGATATAGC
GTTGAGCTGgtgagtccttcacaaaggtgatggagcgacaatcgggttctgacagtcaatagTACACCTAT
GGATGTCCTCGAATCGGAAACTATGCGCTGGCTGAGCATATCACCAGTCAGGGA
TCTGGGGCCAACTTCCGTGTTACACACTTGAACGACATCGTCCCCCGGGTGCCA
CCCATGGACTTTGGATTCAGTCAGCCAAGTCCGGAATACTGGATCACCAGTGGC
AATGGAGCCAGTGTCACGGCGTCGGATATCGAAGTCATCGAGGGAATCAATTCA
ACGGCGGGAAATGCAGGCGAAGCAACGGTGAGCGTTGTGGCTCACTTGTGGTA
CTTTTTTGCGATTTCCGAGTGCCTGCTATAA

SIGNAL SEQUENCE (BOLD)
INTRONS (LOWER CASE)

*FIG. 17.*

SEQ. ID # 4 WITHOUT SIGNAL SEQ

AgtaggtgtgcccgatgtgagatggttggatagcactgatgaagggtgaatagGTGTCTCGACT
TCCACGTTGGATGAGTTGCAATTGTTCGCGCAATGGTCTGCCGCAGCT
TATTGCTCGAATAATATCGACTCGAAAGACTCCAACTTGACATGCACGG
CCAACGCCTGTCCATCAGTCGAGGAGGCCAGTACCACGATGCTGCTG
GAGTTCGACCTgtatgtcactcagatcgcagacatagagcacagctaatttgaacagGACGA
ACGACTTTGGAGGCACAGCCGGTTTCCTGGCCGCGGACAACACCAAC
AAGCGGCTCGTGGTCGCCTTCCGGGGAAGCAGCACGATTGAGAACTG
GATTGCTAATCTTGACTTCATCCTGGAAGATAACGACGACCTCTGCAC
CGGCTGCAAGGTCCATACTGGTTTCTGGAAGGCATGGGAGTCCGCTG
CCGACGAACTGACGAGCAAGATCAAGTCTGCGATGAGCACGTATTCG
GGCTATACCCTATACTTCACCGGGCACAGTTTGGGCGGCGCATTGGCT
ACGCTGGGAGCGACAGTTCTGCGAAATGACGGATATAGCGTTGAGCT
GgtgagtccttcacaaaggtgatggagcgacaatcgggttctgacagtcaatagTACACCTATG
GATGTCCTCGAATCGGAAACTATGCGCTGGCTGAGCATATCACCAGTC
AGGGATCTGGGGCCAACTTCCGTGTTACACACTTGAACGACATCGTCC
CCCGGGTGCCACCCATGGACTTTGGATTCAGTCAGCCAAGTCCGGAA
TACTGGATCACCAGTGGCAATGGAGCCAGTGTCACGGCGTCGGATAT
CGAAGTCATCGAGGGAATCAATTCAACGGCGGGAAATGCAGGCGAAG
CAACGGTGAGCGTTGTGGCTCACTTGTGGTACTTTTTTGCGATTTCCG
AGTGCCTGCTATAA

*FIG. 18.*

CBH1 PROMOTER SEQUENCE

SEQ ID NO 5

```
cagccacttgcagtccgtggaattctcacggtgaatgtaggccttttgagggtaggaattgtcactcaagcaccccaacctcattacg
cctccccatagagttcccaatcagtgagtcatggcactgttctcaaatagattgggagaagttgacttccgcccagagctgaaggtcgc
acaaccgcatgatataggtgcgcaacggcaaaaagcacgtggctcaccgaaaaagcaagatgttgcatctaacatccaggaac
ctggatacatccatcatcacgcacgaccacttgatctgctggtaaactcgtattcgccctaaaccgaagtgcgtggtaaatctacacgtgg
gcccctttcggtatactgcgtgtgtcttctctagttgccattcttttcccttcctctagtgttgaattgttgttgagtccgagctgtaactacctct
gaatctcgagaatggtggactaacgactaccgtcacctgcatcatgtatataatagtgatcctgagaaggggggtttggagcaatgt
ggactttgatgctcatcaaacaagaaggccagagacaatcattcaaaacaccaagcttgctctttgttcggctacgtgaagaacctgtgatactgttgtgtctct
gtgtattttgtgcaacagaggccagagacaatcattcaaaacaccaagcttgctctttgagctacaagaacctggggtatatcta
gagttgaagtcggtaatccgctgtatagtaatacgagtcgcatctaaatactccgagctgctgcgaaccggagaatcgagatgtg
ctggaaagcttcagcgagcggctagagagcaggcactcattccgaaaaaactcggagattccttaagtagcgatgaaccggaataataa
caagcaatacattgagttccgtcctcgacgttgcctgcaatgcaggggtactgagcttgacataactgttccgtacccccacctctctcaaccttgg
taggcaatacattgagttcagcgtacccgtacaagtcgtaatcactattaaccagactgaccggacgtgttgccctcatttgagaaaaatgtc
attgcgatgtgtaatttgcctgctgacgactggggctgttgaagccgaactgtagagttgattgtatcgaactctgctcgtagaggcatgtgt
gaatctgtcgggcaggacacgcctcgaaggttcacgcagcagtcctaaaggttaatgcctaaagaagtcataccagcggctaataattgt
aatgcagcatcactggcatactggcgtgaaaatacaaaccaatggcctaaacgctatttgccaacgctgtgggtgcaacggctaaagcgc
acaatcaagtggctaaacgtaccgtaattgccccaattgggtgatccccaattgggtcgctgttgttccgtgaagtcaacctgaagaagaagctcccacgttgtttctt
cactcagtccaatctcagctggtgatccccaattgggtcgctgttgttccgtgaagtcagcagaagttgacattcaaggagtattgacattagccaggggatgcttgagtgtatc
ggagcgttttgcatcaacccaaggcagtgatgaagacagtgaatgttcactctgatgaagtggttcatttgggtgtacattggctccggcactgaaca
gtgtaaggagttgtctgcgataacgactaagatccggcctttaccagtccggccttggtatgtttgctccggcaatgcaaa
gcaaaagattgagttgaaactgccaagactgccttaccaagcagctggaggtgtgataggcaaatgttcagggccactcatgttcgaat
gtgtaggatcgaacacactgcgcttaccaagcagctgaggtgtgataggcaaatgttcagggccactcatgttcgaat
agaagagaagcttagccaagaacaatagccgataaagatacgctcattaaacggaatgagctagtaggcaaagtcagcgaatgttgt
atataaaggttcgagtcgtccgtgcctccctatgctctcccatctactactcatcatccatcagatcctcaactcagatactcagagagactgtaccactcttgag
gcacagaaacccaatagtcaaccatcacaagttgta
```

FIG. 19.

SEQUENCE LISTING

<160> NUMBER OF SEQ ID NOS: 5

<210> SEQ ID NO 1
<211> LENGTH: 297
<212> TYPE: PRT
<213> ORGANISM: Aspergillus tubingensis

<400> SEQUENCE: 1

Met Phe Ser Gly Arg Phe Gly Val Leu Leu Thr Ala Leu Ala Ala Leu
1               5                   10                  15

Gly Ala Ala Ala Pro Ala Pro Leu Ala Val Arg Ser Val Ser Thr Ser
            20                  25                  30

Thr Leu Asp Glu Leu Gln Leu Phe Ala Gln Trp Ser Ala Ala Ala Tyr
        35                  40                  45

Cys Ser Asn Asn Ile Asp Ser Lys Asp Ser Asn Leu Thr Cys Thr Ala
    50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95

-continued

Asp Asn Thr Asn Lys Arg Leu Val Val Ala Phe Arg Gly Ser Ser Thr
             100                 105                 110

Ile Glu Asn Trp Ile Ala Asn Leu Asp Phe Ile Leu Glu Asp Asn Asp
         115                 120                 125

Asp Leu Cys Thr Gly Cys Lys Val His Thr Gly Phe Trp Lys Ala Trp
     130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                 165                 170                 175

Ala Leu Ala Thr Leu Gly Ala Thr Val Leu Arg Asn Asp Gly Tyr Ser
             180                 185                 190

Val Glu Leu Tyr Thr Tyr Gly Cys Pro Arg Ile Gly Asn Tyr Ala Leu
         195                 200                 205

Ala Glu His Ile Thr Ser Gln Gly Ser Gly Ala Asn Phe Arg Val Thr
     210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                 245                 250                 255

Val Thr Ala Ser Asp Ile Glu Val Ile Glu Gly Ile Asn Ser Thr Ala
             260                 265                 270

Gly Asn Ala Gly Glu Ala Thr Val Ser Val Ala His Leu Trp Tyr
         275                 280                 285

Phe Phe Ala Ile Ser Glu Cys Leu Leu
     290                 295

<210> SEQ ID NO 2
<211> LENGTH: 270
<212> TYPE: PRT
<213> ORGANISM: Aspergillus tubingensis

<400> SEQUENCE: 2

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
                 20                  25                  30

Leu Thr Cys Thr Ala Asn Ala Cys Pro Ser Val Glu Glu Ala Ser Thr
         35                  40                  45

Thr Met Leu Leu Glu Phe Asp Leu Thr Asn Asp Phe Gly Gly Thr Ala
     50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                 85                  90                  95

Leu Glu Asp Asn Asp Asp Leu Cys Thr Gly Cys Lys Val His Thr Gly
             100                 105                 110

Phe Trp Lys Ala Trp Glu Ser Ala Ala Asp Glu Leu Thr Ser Lys Ile
         115                 120                 125

Lys Ser Ala Met Ser Thr Tyr Ser Gly Tyr Thr Leu Tyr Phe Thr Gly
     130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                 165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Val
                245                 250                 255

Ala His Leu Trp Tyr Phe Phe Ala Ile Ser Glu Cys Leu Leu
            260                 265                 270

<210> SEQ ID NO 3
<211> LENGTH: 1045
<212> TYPE: DNA
<213> ORGANISM: Aspergillus tubingensis

<400> SEQUENCE: 3
atgttctctg gacggtttgg agtgcttttg acagcgcttg ctgcgctggg tgctgccgcg      60
ccggcaccgc ttgctgtgcg gagtaggtgt gcccgatgtg agatggttgg atagcactga     120
tgaagggtga ataggtgtct cgacttccac gttggatgag ttgcaattgt tcgcgcaatg     180
gtctgccgca gcttattgct cgaataatat cgactcgaaa gactccaact tgacatgcac     240
ggccaacgcc tgtccatcag tcgaggaggc cagtaccacg atgctgctgg agttcgacct     300
gtatgtcact cagatcgcag acatagagca cagctaattt gaacaggacg aacgactttg     360
gaggcacagc cggtttcctg ccgcgggaca caccaacaa gcggctcgtg gtcgccttcc      420
ggggaagcag cacgattgag aactggattg ctaatcttga cttcatcctg gaagataacg     480
acgacctctg caccggctgc aaggtccata ctggtttctg gaaggcatgg gagtccgctg     540
ccgacgaact gacgagcaag atcaagtctg cgatgagcac gtattcgggc ataccctat      600 acttcaccgg gcacagtttg gcggcgcat tggctacgct gggagcgaca gttctgcgaa      660
atgacggata tagcgttgag ctggtgagtc cttcacaaag gtgatggagc gacaatcggg     720
ttctgacagt caatagtaca cctatggatg tcctcgaatc ggaaactatg cgctggctga    780
gcatatcacc agtcagggat ctggggccaa cttccgtgtt acacacttga acgacatcgt     840
cccccgggtg ccacccatgg actttggatt cagtcagcca gtccggaat actggatcac      900 cagtggcaat ggagccagtg tcacggcgtc ggatatcgaa gtcatcgagg gaatcaattc     960
aacggcggga atgcaggcg aagcaacggt gagcgttgtg gctcacttgt ggtacttttt      1020
tgcgatttcc gagtgcctgc tataa                                            1045

<210> SEQ ID NO 4
<211> LENGTH: 964
<212> TYPE: DNA
<213> ORGANISM: Aspergillus tubingensis

<400> SEQUENCE: 4
agtaggtgtg cccgatgtga gatggttgga tagcactgat gaagggtgaa taggtgtctc      60
gacttccacg ttggatgagt tgcaattgtt cgcgcaatgg tctgccgcag cttattgctc     120
gaataatatc gactcgaaag actccaactt gacatgcacg gccaacgcct gtccatcagt     180
cgaggaggcc agtaccacga tgctgctgga gttcgacctg tatgtcactc agatcgcaga     240

|   |   |
|---|---|
| catagagcac agctaatttg aacaggacga acgactttgg aggcacagcc ggtttcctgg | 300 |
| ccgcggacaa caccaacaag cggctcgtgg tcgccttccg gggaagcagc acgattgaga | 360 |
| actggattgc taatcttgac ttcatcctgg aagataacga cgacctctgc accggctgca | 420 |
| aggtccatac tggtttctgg aaggcatggg agtccgctgc cgacgaactg acgagcaaga | 480 |
| tcaagtctgc gatgagcacg tattcgggct ataccctata cttcaccggg cacagtttgg | 540 |
| gcggcgcatt ggctacgctg ggagcgacag ttctgcgaaa tgacggatat agcgttgagc | 600 |
| tggtgagtcc ttcacaaagg tgatggagcg acaatcgggt tctgacagtc aatagtacac | 660 |
| ctatggatgt cctcgaatcg gaaactatgc gctggctgag catatcacca gtcagggatc | 720 |
| tggggccaac ttccgtgtta cacacttgaa cgacatcgtc ccccgggtgc cacccatgga | 780 |
| ctttggattc agtcagccaa gtccggaata ctggatcacc agtggcaatg agccagtgt | 840 |
| cacggcgtcg gatatcgaag tcatcgaggg aatcaattca acggcgggaa atgcaggcga | 900 |
| agcaacggtg agcgttgtgg ctcacttgtg gtactttttt gcgatttccg agtgcctgct | 960 |
| ataa | 964 |

<210> SEQ ID NO 5
<211> LENGTH: 2236
<212> TYPE: DNA
<213> ORGANISM: Trichoderma reesei

<400> SEQUENCE: 5

|   |   |
|---|---|
| cagccacttg cagtcccgtg gaattctcac ggtgaatgta ggccttttgt agggtaggaa | 60 |
| ttgtcactca agcaccccca acctccatta cgcctccccc atagagttcc caatcagtga | 120 |
| gtcatggcac tgttctcaaa tagattgggg agaagttgac ttccgcccag agctgaaggt | 180 |
| cgcacaaccg catgatatag ggtcggcaac ggcaaaaaag cacgtggctc accgaaaagc | 240 |
| aagatgtttg cgatctaaca tccaggaacc tggatacatc catcatcacg cacgaccact | 300 |
| ttgatctgct ggtaaactcg tattcgccct aaaccgaagt gcgtggtaaa tctacgcgtg | 360 |
| ggccccttte ggtatactge gtgtgtcttc tctaggtgcc attcttttcc cttcctctag | 420 |
| tgttgaattg tttgtgttgg agtccgagct gtaactacct ctgaatctct ggagaatggt | 480 |
| ggactaacga ctaccgtgca cctgcatcat gtatataata gtgatcctga aagggggggt | 540 |
| ttggagcaat gtgggacttt gatggtcatc aaacaaagaa cgaagacgcc tcttttgcaa | 600 |
| agttttgttt cggctacggt gaagaactgg atacttgttg tgtcttctgt gtattttgt | 660 |
| ggcaacaaga ggccagagac aatctattca aacaccaagc ttgctctttt gagctacaag | 720 |
| aacctgtggg gtatatatct agagttgtga agtcggtaat cccgctgtat agtaatacga | 780 |
| gtcgcatcta aatactccga agctgctgcg aacccggaga atcgagatgt gctggaaagc | 840 |
| ttctagcgag cggctaaatt agcatgaaag gctatgagaa attctggaga cggcttgttg | 900 |
| aatcatggcg ttccattctt cgacaagcaa agcgttccgt cgcagtagca ggcactcatt | 960 |
| cccgaaaaaa ctcggagatt cctaagtagc gatggaaccg gaataatata ataggcaata | 1020 |
| cattgagttg cctcgacggt tgcaatgcag gggtactgag cttggacata actgttccgt | 1080 |
| accccacctc ttctcaacct ttggcgtttc cctgattcag cgtacccgta caagtcgtaa | 1140 |
| tcactattaa cccagactga ccggacgtgt tttgcccttc atttggagaa ataatgtcat | 1200 |
| tgcgatgtgt aatttgcctg cttgaccgac tggggctgtt cgaagcccga atgtaggatt | 1260 |
| gttatccgaa ctctgctcgt agaggcatgt tgtgaatctg tgtcgggcag acacgcctc | 1320 |
| gaaggttcac ggcaagggaa accaccgata gcagtgtcta gtagcaacct gtaaagccgc | 1380 |

```
aatgcagcat cactggaaaa tacaaaccaa tggctaaaag tacataagtt aatgcctaaa    1440
gaagtcatat accagcggct aataattgta caatcaagtg gctaaacgta ccgtaatttg    1500
ccaacggctt gtggggttgc agaagcaacg gcaaagcccc acttccccac gtttgtttct    1560
tcactcagtc caatctcagc tggtgatccc ccaattgggt cgcttgtttg ttccggtgaa    1620
gtgaaagaag acagaggtaa gaatgtctga ctcggagcgt tttgcataca accaagggca    1680
gtgatggaag acagtgaaat gttgacattc aaggagtatt tagccaggga tgcttgagtg    1740
tatcgtgtaa ggaggtttgt ctgccgatac gacgaatact gtatagtcac ttctgatgaa    1800
gtggtccata ttgaaatgta aagtcggcac tgaacaggca aaagattgag ttgaaactgc    1860
ctaagatctc gggccctcgg gccttcggcc tttgggtgta catgtttgtg ctccgggcaa    1920
atgcaaagtg tggtaggatc gaacacactg ctgcctttac caagcagctg agggtatgtg    1980
ataggcaaat gttcaggggc cactgcatgg tttcgaatag aaagagaagc ttagccaaga    2040
acaatagccg ataaagatag cctcattaaa cggaatgagc tagtaggcaa agtcagcgaa    2100
tgtgtatata taaaggttcg aggtccgtgc ctccctcatg ctctccccat ctactcatca    2160
actcagatcc tccaggagac ttgtacacca tcttttgagg cacagaaacc caatagtcaa    2220
ccatcacaag tttgta                                                   2236
```

METHOD OF PRODUCING A LIPOLYTIC ENZYME

CROSS-REFERENCE TO RELATED APPLICATIONS

This application claims priority to U.S. application Ser. No. 13/265,712, entitled "METHOD OF PRODUCING A LIPOLYTIC ENZYME," filed Dec. 6, 2011, which is a national stage Application of and claims priority to PCT Application No. PCT/IB2010/051802, entitled "METHOD OF PRODUCING A LIPOLYTIC ENZYME," filed Apr. 23, 2010, which claims priority to U.S. Provisional Application No. 61/172,272, filed Apr. 24, 2009 and Great Britain Application No. 0908770.1, filed May 20, 2009, each of which is expressly incorporated by reference herein in its entirety.

FIELD OF THE PRESENT INVENTION

The present invention relates to a method for the production of a lipolytic enzyme in *Trichoderma reesei* and the lipolytic enzyme obtainable there from. In addition, the present invention relates to the use of *Trichoderma* to express a lipolytic enzyme.

SEQUENCE LISTING

A text file in compliance with ASCII and having a ".txt" extension has been electronically submitted via EFS-Web. The text file named "Sequence Listing-Method" was created on Oct. 20, 2011, and is 11,152 bytes. The text file is expressly incorporated by reference herein in its entirety.

BACKGROUND

Lipases (EC 3.1.1.3), which can be defined as carboxylesterases which catalyze the hydrolysis of acylglycerols, are physiologically very important enzymes as one of the three major digestive enzymes together with amylases and proteases. They hydrolyse lipids to glycerol and fatty acids, but can also function in esterification or transesterification reactions.

Lipases have applications in several industrial processes such as processing of oils and fats, detergent manufacturing, paper processing and in the cheese making and baking industries.

WO 98/45453 discloses a lipolytic enzyme (and variants thereof) derived from the filamentous fungus *Aspergillus tubingensis*. This enzyme is sometimes referred to as "lipase 3". WO 98/45453 characterizes several of the physicochemical characteristics of lipase 3. Uses of this lipolytic enzyme for improving the properties of bread were also described, in particular for improving the properties of bread.

WO 98/45453 also described the cloning and expression of lipase 3 and its variants in *Aspergillus tubingensis*. It was found that this lipolytic enzyme could be overexpressed in *Aspergillus tubingensis*, however the enzyme was overglycosylated in *A. tubingensis* which, in some situations, can decrease its activity.

There is a need for a method for the production of lipase 3 and its variants and other lipolytic enzymes on a commercial scale and using expression hosts which provide high levels of protein expression and yield. In addition, there is also a need to overcome the problem of decreased enzyme activity due to overglycosylation of the lipolytic enzyme as seen for example when it is overexpressed in *A. tubingensis*.

SUMMARY

It has surprisingly been found that *Trichoderma reesei* is a highly efficient expression host for lipolytic enzymes—in particular lipase 3 and its variants and other lipolytic enzymes.

Accordingly, in a first aspect of the present invention there is provided a method of producing a lipolytic enzyme comprising the steps of:

(i) providing a *Trichoderma reesei* cell comprising a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which is at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions; and (ii) culturing the cell under conditions to allow for expression of said heterologous nucleotide sequence(s) encoding said lipolytic enzyme.

In a further aspect of the present invention there is provided a method of producing a lipolytic enzyme comprising the steps of:

(i) transfecting or transforming a *Trichoderma reesei* cell with a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions;

(ii) culturing the cell under conditions to allow for expression of said heterologous nucleotide sequence(s) encoding said lipolytic enzyme.

In a further aspect of the present invention there is provided a method of producing a lipolytic enzyme comprising the steps of:

(i) transfecting or transforming a *Trichoderma reesei* cell with a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions;

(ii) repeating step (i) on the cell to sequentially transfect or transform the cell with at least one additional heterologous nucleotide sequence as defined in (i)(a), (i)(b) or (i)(c) (e.g. such as a heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2); and (iii) culturing the cell under conditions to allow for expression of said heterologous nucleotide sequence(s) encoding said lipolytic enzyme.

The present invention yet further provides a lipolytic enzyme obtainable by a method of the present invention.

There is also provided by the present invention, a foodstuff for human consumption comprising said lipolytic enzyme obtainable by a method of the present invention.

The present invention yet further provides a transformed or transfected *Trichoderma reesei* cell comprising:

a) at least one heterologous nucleotide sequence encoding a lipolytic enzyme protein having at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 40% sequence identity to SEQ ID NO: 3 or SEQ ID NO: 4 or the complement of any thereof under stringent conditions.

In another aspect the present invention provides an expression vector comprising:

i) at least one nucleotide sequence which nucleotide sequence:

a) encodes a lipolytic enzyme protein having at least 40% sequence identity to SEQ ID NO: 1 or 2; and/or b) encodes a lipolytic enzyme and comprises the nucleotide sequence shown as SEQ ID NO: 3 or SEQ ID NO: 4 or a nucleotide sequence which is at least 40% sequence identity to SEQ ID NO: 3 or SEQ ID NO: 4; and/or c) encodes a lipolytic enzyme wherein the nucleotide sequence comprises a nucleotide sequence which hybridizes to SEQ ID NO: 3 or SEQ ID NO: 4 or a nucleotide sequence which is at least 40% sequence identity to SEQ ID NO: 3 or SEQ ID NO: 4 or the complement of any thereof under stringent conditions; and ii) at least one cellobiohydrolase promoter, wherein said at least one nucleotide sequence is under the control of said at least one cellobiohydrolase promoter.

In another aspect of the present invention, there is provided a use of a *Trichoderma reesei* cell in the expression of a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which is at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 40% sequence identity to SEQ ID NO: 3 or SEQ ID NO: 4 or the complement of any thereof under stringent conditions;

for improving one or more of the following: expression of the lipolytic enzyme, glycosylation of the lipolytic enzyme, enzyme activity or yield.

Surprisingly, we have found that *Trichoderma reesei* is capable of producing the lipolytic enzymes in significantly high yields.

Furthermore, we have found that the lipolytic enzymes produced by the methodology of the present invention are surprisingly not overglycosylated and therefore have good enzyme activity.

Bradner et al. (in Current Genetics, 44: 224-230, (2003)) used *Trichoderma reesei* as an expression host organism in their search for previously unknown lipolytic enzymes. A lipase from an Antarctic isolate of *Penicillium allii* was cloned and expressed in *Trichoderma reesei*. Bradner et al. concluded that the methods described would be useful for prospecting for potentially novel lipase genes but no suggestion was made that *T. reesei* could be used for overexpression of proteins.

In another aspect the present invention provides a method of producing a lipolytic enzyme comprising the steps of:

(i) providing a transformed or transfected *Trichoderma reesei* cell comprising at least one heterologous nucleotide sequence encoding a lipolytic enzyme;

(ii) culturing the cell at a pH 4 to pH 5.5 under conditions to allow for expression of said heterologous nucleotide sequence(s) encoding said lipolytic enzyme;

(iii) isolating, purifying or concentrating the enzyme in a medium at pH 5.5 to pH 6.5.

In this aspect, preferably the lipolytic enzyme:

a) comprises an amino acid sequence shown as SEQ ID NO: 1 or SEQ ID NO: 2 or comprises an amino acid sequence which has at least 40% sequence identity to SEQ ID NO: 1 or 2; and/or b) is encoded by a nucleotide comprising the sequence shown as SEQ ID NO: 3 or SEQ ID NO: 4 or comprising a nucleotide sequence which has at least 40% sequence identity to SEQ ID NO: 3 or SEQ ID NO: 4; and/or c) is encoded by a nucleotide sequence comprising a nucleotide sequence which hybridizes to SEQ ID NO: 3 or SEQ ID NO: 4 or comprises a nucleotide sequence which is at least 40% sequence identity to SEQ ID NO: 3 or SEQ ID NO: 4 or the complement of any thereof under stringent conditions.

BRIEF DESCRIPTION OF THE FIGURES

The present invention is further illustrated by reference to the accompanying figures in which:

FIG. 1 shows a model of the predicted translational modifications in a lipolytic enzyme (sometimes referred to herein as "lipase 3") and shown herein as SEQ ID No. 2; active site residues are shown in a circle—see Ser146, Asp201, His258; there are 7 cysteine residues and 4 are involved in disulfide bonds, shown as a dashed line and as a solid line above the residues; there are 2 sites for N-linked glycosylation, namely N32 & N242 which are shown in bold and are underlined (the latter, namely N242, is near to the His active site). NOTE: the numbering in this Figure relates to the lipolytic enzyme shown as SEQ ID No. 2 without the signal peptide of 27 amino acids—therefore when referring to the lipolytic enzyme shown in SEQ ID No. 1 (i.e. with the signal peptide) the numbering in respect of the active site residues needs to be adjusted by adding 27 amino acids.

FIG. 8 shows the yield of the lipolytic enzyme (lipase 3) protein in the fermentation broth when the lipolytic enzyme is expressed in different expression hosts. Yield is expressed as a % increase in yield in each organism:
1 *Aspergillus tubingensis*;
2 *Pichia pastoris*;
3 *Hansenula polymorpha*;
4 *Trichoderma reesei*.

FIG. 15 shows the amino acid sequence (SEQ ID No. 1) of a lipolytic enzyme from *Aspergillus tubingensis* wherein the endogenous signal peptide is shown in bold.

FIG. 16 shows the amino acid sequence (SEQ ID No. 2) of a lipolytic enzyme from *Aspergillus tubingensis* which is the same as SEQ ID No. 1 except that the endogenous signal peptide has been removed.

FIG. 17 shows the nucleotide sequence encoding an *Aspergillus tubingensis* lipolytic enzyme (as shown in SEQ ID No. 1) including the signal sequence—the nucleotide sequence is a genomic DNA sequence (and has been designated as SEQ ID No. 3. The signal sequence is shown in bold and the introns are shown in lower case.

FIG. 18 shows the nucleotide sequence encoding an *Aspergillus tubingensis* lipolytic enzyme (as shown in SEQ ID No. 2) not including the signal sequence—the nucleotide sequence is a genomic DNA sequence (and has been designated as SEQ ID No. 4. The introns are shown in lower case.

FIG. 19 shows the sequence of the cellobiohydrolase 1 gene (cbh1) promoter designated SEQ ID No. 5.

DETAILED DESCRIPTION

Figure 2:
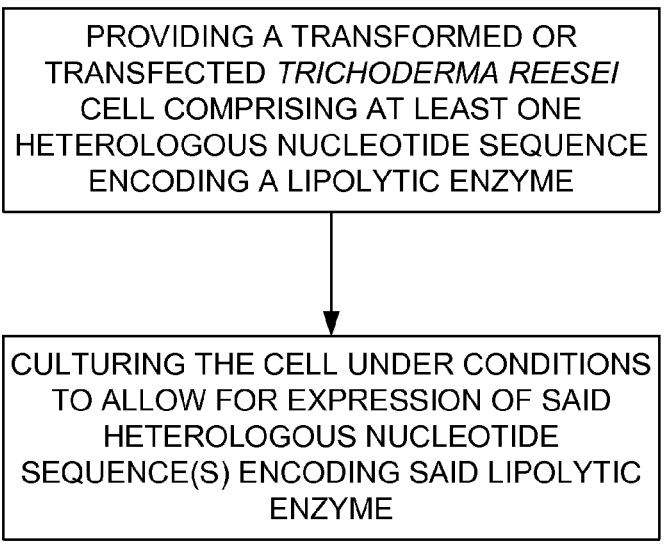
FIG. 2 shows a schematic of the method of the present invention.

Preferably, the heterologous nucleotide sequence is operably connected (directly or indirectly) to a promoter sequence such that the heterologous nucleotide sequence is under the control of the promoter sequence.

The promoter sequence may be any suitable promoter—such as a promoter that is naturally associated with the nucleotide sequence coding for the lipolytic enzyme and/or a heterologous promoter, such as a cellobiohydrolase 1 promoter sequence or Tef promoter or a glucoamylase promoter. Other *Trichoderma* promoter sequences derived from stp (U.S. Ser. No. 12/193,614), cbh2, egl1, egl2, gpd1 genes, can be linked to the nucleotide sequence of the lipolytic enzyme.

For some embodiments the nucleotide sequence coding for the lipolytic enzyme may include one or more introns.

For some embodiments the nucleotide sequence coding for the lipolytic enzyme is a genomic sequence.

For some embodiments the nucleotide sequence coding for the lipolytic enzyme is a cDNA sequence.

The method of the present invention may comprise the additional step of isolating and/or purifying and/or recovering the lipolytic enzyme.

For some embodiments the level of expressed lipolytic enzyme is high enough so that one can use the broth medium into which the enzyme has been secreted (preferably after removal of the cell(s)) or in a concentrate form (preferably after removal of the cell(s)).

Therefore, in a preferred aspect, the method of the present invention includes the following additional step(s) of isolating and/or purifying and/or recovering the lipolytic enzyme.

In a more preferred aspect, the method of the present invention includes the following additional step(s) of removing the cell(s) from the medium (e.g. broth) into which the enzyme has been secreted.

In a more preferred aspect, the method of the present invention includes the following additional step(s) of removing the cell(s) from the medium (e.g. broth) into which the enzyme has been secreted; and then concentrating the medium.

The cell(s) may be removed from the medium via suitable separation techniques—e.g. suitable filtration techniques and/or centrifugation techniques. A particular example is use of ultra-filtration to prepare UFCs (ultra-filtration concentrates).

In one embodiment, the pH of the medium for culturing is about pH 4 to about 5.5, preferably about pH 4.

In one embodiment, the pH of the medium for culturing is about pH 4.

In a preferred embodiment, prior to the isolation and/or purification and/or concentration of the enzyme, the pH of the medium is raised at the end of the fermentation run when sufficient levels of the secreted, soluble enzyme are reached.

In one embodiment, the pH of the medium for isolating and/or purifying and/or concentrating the enzyme is above pH 5.5 to about pH 6.5.

Thus, in one embodiment, the pH of the medium for culturing is about pH 4 and then the pH of the medium is raised such that the pH of the medium for isolating and/or purifying and/or concentrating the enzyme is above pH 5.5 to about pH 6.5.

Thus, in one embodiment, the pH of the medium for culturing is about pH 4 and then the pH of the medium is raised such that the pH of the medium for isolating and/or purifying and/or concentrating the enzyme is above about pH 6 to about pH 6.5.

In a preferred embodiment, the pH of the medium for culturing is about pH 4.5 and then the pH of the medium is raised such that the pH of the medium for isolating and/or purifying and/or concentrating the enzyme is about pH 6.

Preferably the *Trichoderma reesei* cell is provided by transforming it with, or is transformed with, the nucleotide sequence using electroporation, such as by the electroporation methodology disclosed in WO 2008/153712 A2.

In another embodiment, the *Trichoderma reesei* cell may be provided by transforming it with, or may be transformed with, the nucleotide sequence using biolistic transformation.

Suitably there may be at least one heterologous nucleotide sequence encoding the lipolytic enzyme in the *Trichoderma reesei* cell. In some embodiments, there may be two or more copies (i.e. multiple copies) of the or each heterologous nucleotide sequence encoding the lipolytic enzyme according to the present invention in the *Trichoderma reesei* cell. For example, in one embodiment there may be at least two nucleotide sequences encoding the lipolytic enzyme in the *Trichoderma reesei*. In other embodiments there may be at least three, such as at least four, such as at least five, or such as at least six heterologous nucleotide sequences encoding said lipolytic enzyme. Suitably there may be up to about six, preferably up to about seven, preferably up to about eight, preferably up to about ten heterologous nucleotide sequences encoding the lipolytic enzyme in the *Trichoderma reesei* cell. In some embodiments each heterologous nucleotide sequence is associated with and is under the control of a promoter. Suitably each heterologous nucleotide sequence may have a separate promoter associated with it and be under the control of that promoter. The promoters may be the same or different.

Thus, in one embodiment the *Trichoderma reesei* cell may comprise or be transfected or transformed with at least 2 heterologous nucleotide sequences encoding the lipolytic enzyme. In another embodiment the *Trichoderma reesei* cell may comprise or be transfected or transformed with at least 3, or at least 4, or at least 5 or at least 6 heterologous nucleotide sequences encoding the lipolytic enzyme. In one embodiment there is up to about 6 heterologous nucleotide sequences encoding the lipolytic enzyme in accordance with the present invention. In some embodiments there may be up to about 10 heterologous nucleotide sequences encoding the lipolytic enzyme in accordance with the present invention. In some embodiments each heterologous nucleotide sequence is associated with and under the control of a promoter. Suitably each heterologous nucleotide sequence may have separate promoter associated with it and be under the control of that promoter.

Suitably, the (or each) heterologous nucleotide sequence may comprise a nucleotide sequence which encodes a signal peptide, which nucleotide sequence encoding said signal peptide is operably linked to said nucleotide sequence encoding said lipolytic enzyme. If there are multiple heterologous nucleotide sequences and wherein more than one has a signal sequence associated therewith, then the signal sequences may be the same or different.

Suitably the lipolytic enzyme may comprise an endogenous or exogenous signal peptide. When the signal peptide is endogenous—it means that the signal peptide is that which is naturally linked with the lipolytic enzyme when produced naturally. For example, the signal peptide may be the signal peptide in *Aspergillus tubingensis* which is naturally linked with the lipolytic enzyme when found in *Aspergillus tubingensis*.

The term "heterologous" as used herein means that it is does not occur naturally in the *Trichoderma reesei* cell. In other words, it is exogenous to the *Trichoderma reesei* cell. For example the term "heterologous nucleotide sequence" as used herein means that the nucleotide sequence does not occur naturally in the *Trichoderma reesei* cell. In other words, the nucleotide sequence is exogenous to the *Trichoderma reesei* cell. The term also includes multiple copies of the naturally occurring sequence as such additional multiple copies would be heterologous.

In one embodiment preferably the heterologous nucleotide sequence is obtained or obtainable from a microorganism, particularly a fungi.

In one embodiment preferably the heterologous nucleotide sequence is obtained or obtainable from *Aspergillus*, particularly *Aspergillus tubingensis*.

In a further aspect of the present invention there is provided a method of producing a lipolytic enzyme comprising the steps of:
(i) providing a *Trichoderma reesei* cell comprising
  a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which is at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions; and (ii) culturing the cell under conditions to allow for expression of said heterologous nucleotide sequence(s) encoding said lipolytic enzyme; and wherein said *Trichoderma reesei* cell has at least two genes encoding non-lipolytic enzymes suppressed.

In a further aspect of the present invention there is provided a method of producing a lipolytic enzyme comprising the steps of:

(i) transfecting or transforming a *Trichoderma reesei* cell with a) at least one heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions;

(ii) culturing the cell under conditions to allow for expression of said heterologous nucleotide sequence(s) encoding said lipolytic enzyme; and wherein said *Trichoderma reesei* cell has at least two genes encoding non-lipolytic enzymes suppressed.

In a further aspect of the present invention there is provided a method of producing a lipolytic enzyme comprising the steps of:

(i) transfecting or transforming a *Trichoderma reesei* cell with a) at least one heterologous nucleotide sequence encoding a lipolytic enzyme comprising an amino acid sequence shown as SEQ ID NO: 1 or SEQ ID NO: 2 or an amino acid sequence which has at least 30% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which has at least 40% sequence identity to SEQ ID NO: 3 or SEQ ID NO: 4 or the complement of any thereof under stringent conditions;

(ii) repeating step (i) on the cell to sequentially transfect or transform the cell with at least one additional heterologous nucleotide sequence as defined in (i)(a), (i)(b) or (i)(c) (e.g. such as a heterologous nucleotide sequence encoding a lipolytic enzyme comprising an amino acid sequence shown as SEQ ID NO: 1 or SEQ ID NO: 2 or an amino acid sequence which has at least 40% sequence identity to SEQ ID NO: 1 or 2); and (iii) culturing the cell under conditions to allow for expression of said heterologous nucleotide sequence(s) encoding said lipolytic enzyme; and wherein said *Trichoderma reesei* cell has at least two genes encoding non-lipolytic enzymes suppressed.

The present invention yet further provides a lipolytic enzyme obtainable by the methods of the present invention.

There is also provided by the present invention, a foodstuff for human consumption comprising said lipolytic enzyme obtainable by a method of the present invention.

The present invention yet further provides a transformed or transfected *Trichoderma reesei* cell comprising:

a) at least one heterologous nucleotide sequence encoding a lipolytic enzyme protein having at least 40% sequence identity to SEQ ID NO: 1 or 2; and/or b) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 40% sequence identity to SEQ ID NO: 3 or SEQ ID NO: 4; and/or c) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 40% sequence identity to SEQ ID NO: 3 or SEQ ID NO: 4 or the complement of any thereof under stringent conditions; and wherein said *Trichoderma reesei* cell has at least two genes encoding non-lipolytic enzymes suppressed.

Preferably, at least three genes encoding non-lipolytic enzymes suppressed.

Preferably, at least four genes encoding non-lipolytic enzymes suppressed.

"Suppressed" means that the cell does not express the relevant non-lipolytic enzyme at the same level as the non-transformed/transfected cell. In some embodiments, "suppressed" means that the cell does not express the relevant non-lipolytic enzyme. The suppression may be brought about by techniques known in the art, such as by deletions.

Preferably, at least one of the genes encoding a non-lipolytic enzyme that is suppressed is a cellulase gene.

Preferably, at least two of the genes encoding a non-lipolytic enzyme that is suppressed are cellulase genes.

An example of at least one of the genes encoding a non-lipolytic enzyme that is suppressed is a gene encoding a cellobiohydrolases (e.g. CBHI or CBHII).

Another example of at least one of the genes encoding a non-lipolytic enzyme that is suppressed is a gene encoding an endoglucanases (e.g. EGI and EGII).

In some embodiments the *Trichoderma reesei* cell of the present invention is a cell in which the endogenous genes encoding one or both cellobiohydrolases (CBHI and CBHII) and/or one or both of the endoglucanases (EGI and EGII) are deleted or disrupted. Suitably the *Trichoderma reesei* cell may be a non-GMM cell or derivative thereof, for example a derivative of the strain RL-P37. Suitably the *Trichoderma reesei* cell may be a derivative of the strain RL-P37 that is produced using the method set out in Example 10.

In some embodiments, the heterologous nucleotide sequence may encode a lipolytic enzyme comprising an amino acid sequence having at least 30%, at least 35%, at least 40%, at least 45%, at least 50%, at least 55%, at least 60%, at least 65% at least 70%, at least 75%, at least 80%, at least 85%, at least 90%, at least 95% or at least 98% sequence identity to SEQ ID NO: 1 or SEQ ID No. 2 or a sequence comprising one or several amino acid additions, deletions or substitutions compared to SEQ ID NO: 1 or SEQ ID No. 2.

In some embodiments the heterologous nucleotide sequence may encode a lipolytic enzyme and comprises a nucleotide sequence having at least 30%, at least 35%, at least 40%, at least 45%, at least 50%, at least 55%, at least 60%, at least 65% at least 70%, at least 75%, at least 80%, at least 85%, at least 90%, at least 95% or at least 98% sequence identity to SEQ ID NO: 3 or SEQ ID No. 4 or a sequence comprising one or several nucleotide additions, deletions or substitutions compared to SEQ ID NO: 3 or SEQ ID No. 4.

Preferably, the heterologous nucleotide sequence encodes a lipolytic enzyme comprising an amino acid sequence having at least 40%, at least 45%, at least 50%, at least 55%, at least 60%, at least 65%, at least 70%, at least 75%, at least 80%, at least 85%, at least 90%, at least 95% or at least 98% sequence identity to SEQ ID NO: 1 or SEQ ID No. 2 or a sequence comprising one or several amino acid additions, deletions or substitutions compared to SEQ ID NO: 1 or SEQ ID No. 2.

Preferably, the heterologous nucleotide sequence encodes a lipolytic enzyme and comprises a nucleotide sequence having at least 40%, at least 45%, at least 50%, at least 55%, at least 60%, at least 65%, at least 70%, at least 75%, at least 80%, at least 85%, at least 90%, at least 95% or at least 98% sequence identity to SEQ ID NO: 3 or SEQ ID No. 4 or a sequence comprising one or several nucleotide additions, deletions or substitutions compared to SEQ ID NO: 3 or SEQ ID No. 4.

The amino acid sequence identity of a number of lipolytic enzymes to the lipase from *Aspergillus tubingensis* having the sequence shown in SEQ ID NO: 3 (also called herein lipase 3) are shown in Table 1 below.

TABLE 1

Lipolytic enzymes with sequence identity to the lipolytic enzyme from *Aspergillus tubingensis* (lipase 3).

| Lipases from different fungi | Accession No. | Amino acid sequence identity % |
| --- | --- | --- |
| A. niger CBS 513.88 | XP_001397501.1 | 93 |
| Aspergillus niger | ABG73613.1 | 93 |
| Aspergillus niger | ABG37906.1 | 93 |
| Aspergillus nidulans FGSCA4 | XP_681315.1 | 61 |
| Aspergillus clavatus NRRL 1 | XP_001276337.1 | 57 |
| Neosartorya fischeri NRRL 181 | XP_001266329.1 | 60 |
| Aspergillus fumigatus Af293 | XP_748138.1 | 59 |
| Aspergillus oryzae RIB40 | XP_001818694.1 | 56 |
| Aspergillus terreus NIH2624 | XP_001218444.1 | 54 |
| Penicillium chrysogenum Wisconsin 54-1255 | CAP96359.1 | 55 |
| Aspergillus niger | ABG73614.1 | 54 |
| Aspergillus niger | XP_001393532.1 | 53 |
| Thermomyces lanuginosus | O59952.1 | 50 |
| Penicillium marneffei ATCC 18224 | XP_002147144.1 | 49 |
| Aspergillus oryzae R | XP_001824529.1 | 44 |
| Phaeosphaeria nodorum SN15 | XP_001796872.1 | 45 |
| Penicillium cyclopium | P61869.1 | 42 |
| Penicillium camemberti. | 1TIA_A | 42 |

The *Trichoderma reesei* host cell used in the present invention may be any *Trichoderma reesei* cell. The cell may be considered to be a wild type *Trichoderma reesei* cell. The *Trichoderma reesei* cell may be one from which genes encoding one or more secreted cellobiohydrolases (CBHI or CBHII) has/have been deleted or disrupted so that they are not expressed. Suitably the *Trichoderma reesei* cell may be a non-genetically modified cell or derivative thereof, for example a derivative of the strain RL-P37. Suitably the *Trichoderma reesei* cell may be a derivative of the strain RL-P37 that is produced using the method set out in Example 10.

The present invention may be carried out in a fermentor which may comprise about 3 liters to about 20 liters culture media. In another embodiment the present invention is carried out as a 10-16 liter, preferably a 14 liter scale fermentation. In one embodiment, preferably the fermentation is carried out with more than about 12 liters, preferably more than about 14 liters.

The *Trichoderma reesei* host cell is preferably suitable for use in large scale fermentation.

In preferred embodiments, the present invention is carried out on a commercial scale. In this respect, the fermentation of the present invention is carried out at more than about 50,000 liters scale, preferably more than about 80,000 liters scale, preferably at more than about 200,000 liter scale fermentation.

In one embodiment the total protein produced by the method of the present invention is well in excess of about 20 g/liter.

Of the total protein produced in the present invention the majority is the desired lipolytic enzyme. In one embodiment the total secreted protein produced by the method of the present invention comprises at least 50% of the desired lipolytic enzyme. In one embodiment the total secreted protein produced by the method of the present invention comprises at least 60% of the desired lipolytic enzyme. In one embodiment the total secreted protein produced by the method of the present invention comprises at least 70% of the desired lipolytic enzyme. In one embodiment the total secreted protein produced by the method of the present invention comprises at least 80% of the desired lipolytic enzyme.

Suitably the present invention may comprise selection of transformants which have been screened for production of the lipolytic enzyme (high producers of the desired enzyme are preferentially selected).

In one embodiment suitably the present invention may comprise a first transformation step wherein a *Trichoderma reesei* cell is transformed with at least one heterologous nucleotide sequence encoding the lipolytic enzyme defined herein, selection of transformants which have been screened for production of the lipolytic enzyme (high producers of the desired enzyme are preferentially selected), and a second transformation step (i.e. retransformation step) of a selected transformant with at least one heterologous nucleotide sequence encoding the lipolytic enzyme defined herein, followed by further selection of new transformants which have been screened for production of the lipolytic enzyme (high producers of the desired enzyme are preferentially selected).

In some embodiments the lipolytic enzyme produced by the present invention maybe glycosylated. In some embodiments, the lipolytic enzyme may be N-glycosylated at N32 (when numbered using SEQ ID NO: 2) or at an equivalent position for other lipolytic enzymes according to the invention. This aspect may impart significant advantages in that the activity of the enzyme is not disrupted or reduced by glycosylation of the enzyme. Without wishing to be bound by theory, reduction in activity of the lipolytic enzyme can be seen when it is produced in other hosts such as *A. tubingensis* and is thought to be due to over-glycosylation of the enzyme at at least the N242 site.

The lipolytic enzyme produced by the present invention is therefore distinguishable from the lipolytic enzyme produced in other hosts, e.g. *A. tubingensis*, because of the degree of glycosylation of the enzyme, particularly at the N32 site. In some embodiments of the present invention the enzyme has glycosylation at, at least, the N32 site.

Suitably the lipolytic enzyme may be produced with a signal peptide. In other words the heterologous nucleotide sequence used in the present invention comprises a portion thereof which encodes a signal peptide.

The signal peptide may be used to direct secretion of the lipolytic enzyme through a particular cell membrane. The signal peptide sequences may be endogenous or exogenous to the lipolytic enzyme coding sequence. For instance, the signal peptide may be the signal peptide which is endogenous to the lipolytic enzyme is *Aspergillus tubingensis*. Alternatively, the coding sequence for the signal peptide may be obtained (or obtainable) from a cellobiohydrolase gene of *Trichoderma reesei*.

However, any signal peptide coding sequence capable of directing the expressed lipolytic enzyme into the secretory pathway of a *Trichoderma reesei* cell of choice may be used.

When we refer to improving one or more of the following: expression of the lipolytic enzyme, glycosylation of the lipolytic enzyme, enzyme activity and/or yield this is compared with conventional methods of expressing this lipolytic enzyme. For example, in the present invention there is provided an improved expression of the lipolytic enzyme, glycosylation of the lipolytic enzyme, enzyme activity and/or yield compared with production of the lipolytic enzyme in another host organism (i.e. a host organism other than *T. reesei*). In particular, there is an improved expression of the lipolytic enzyme, glycosylation of the lipolytic enzyme, enzyme activity and/or yield of the lipolytic enzyme by the present invention (i.e. produced in the *Trichoderma reesei* cell) as compared with expression of the same lipolytic enzyme in an *Aspergillus tubingensis* cell (for example as taught in WO98/45453, as incorporated herein by reference).

The term "improved glycosylation" as used herein means that, preferably, glycosylation occurs at N32 (when numbered using SEQ ID NO: 2). Without wishing to be bound by theory, in some situations, the lipolytic enzyme produced in host cells other than *T. reesei* (and particularly in *Aspergillus tubingensis* (e.g. as taught in WO98/45453)) may be glycosylated (or overglycosylated), particularly at N242. Therefore, the lipolytic enzyme produced in host cells other than *T. reesei* and particularly in *Aspergillus tubingensis* (e.g. as taught in WO98/45453) may be glycosylated at both N32 and N242 sites. However, and without wishing to be bound by theory, the N242 site is in the vicinity of one of the active site residues, namely His258 of SEQ ID No. 2. Thus, it is believed that glycosylation (or overglycosylation) at the N242 site can lead to a reduced activity (i.e. lipase activity) of the enzyme. The lipolytic enzyme of the present invention does not have reduced activity. Glycosylation of the lipolytic enzyme of the present invention may occur at the N32 site which is away from the active site residues, such as His258.

The term "improved enzyme activity" as used herein means that the activity is the same as or greater than the lipase activity of the lipolytic enzyme produced naturally by *Aspergillus tubingensis*.

By enzyme activity we mean at least lipase activity. Enzyme activity (e.g. lipase activity) can be measured using the relevant protocols set out below in the Examples section.

It has been surprisingly found that the lipolytic enzyme produced in accordance with the present invention is easy to isolate from the medium into which it has been excreted—i.e. the culture (fermentation) broth—as high expression levels are obtained. FIG. 2 shows a schematic for the method of the present invention.

Thus, according to a preferred aspect of the present invention, the method of the present invention may involve one or more of the following steps to the medium into which the enzyme of the present invention has been secreted following culturing of the cell: diluting the medium (preferably with water); separating the cell(s) from the medium; concentrating the medium (preferably wherein said medium is cell-free); granulating said medium (preferably wherein said medium is cell-free).

In a preferred aspect of the present invention, the method of the present invention involves the following steps to the medium into which the enzyme of the present invention has been secreted following culturing of the cell: diluting the medium (preferably with water); separating the cell(s) from the medium; concentrating the medium (preferably wherein said medium is cell-free); and optionally granulating said medium (preferably wherein said medium is cell-free).

In a preferred aspect of the present invention, the method of the present invention involves the following steps to the medium into which the enzyme of the present invention has been secreted following culturing of the cell: diluting the medium (preferably with water); separating the cell(s) from the medium; concentrating the medium (preferably wherein said medium is cell-free); and granulating said medium (preferably wherein said medium is cell-free).

In a preferred aspect of the present invention, the method of the present invention involves the following steps to the medium into which the enzyme of the present invention has been secreted following culturing of the cell: diluting the medium with water; separating the cell(s) from the medium; concentrating the medium wherein said medium is cell-free; and optionally granulating said medium wherein said medium is cell-free.

In a preferred aspect of the present invention, the method of the present invention involves the following steps to the medium into which the enzyme of the present invention has been secreted following culturing of the cell: diluting the medium with water; separating the cell(s) from the medium; concentrating the medium wherein said medium is cell-free; and granulating said medium wherein said medium is cell-free.

According to further aspects of the present invention the enzyme of the present invention is then used in a method to prepare a food or foodstuff intended for human consumption said method comprising admixing said enzyme with a suitable food or foodstuff ingredient. Preferably, said enzyme is in the medium into which the enzyme of the present invention has been secreted following culturing of the cell. Preferably said medium is cell-free (i.e. the cell(s) have been separated from the medium). Preferably said medium is concentrated. In some embodiments, preferably the medium is granulated.

Preferably the lipase precipitates out of solution in the fermentation broth. Preferably, the lipase precipitate is re-solubilised by pH adjustment. Preferably the pH is adjusted to a pH above the pH of the fermentation broth.

Advantages

In addition to the advantages mentioned above, another advantage of the present invention is that it enables commercial scale production of the lipolytic enzyme. The method of the present invention allows for the lipolytic enzyme to be produced in a high yield.

One advantage of the present invention is that it has surprisingly been found that it is possible to go directly from the transformation and screening step (i.e. say from the microtitre plate) directly to large scale fermentation (e.g. at least 14 liter fermentation). This is surprisingly possible because the screening step (particularly the microtitre plate results) are highly predictive of good performance in the large scale fermentation. This contrasts with conventional methods where it is often necessary to cultivate the strain in flasks before moving to larger scale fermentation) This has significant advantages in shortening the production time and/or simplifying the overall procedure and/or reducing costs.

A further advantage of the present invention is that it provides an enhanced/increased expression and/or an improved yield of the lipolytic enzyme compared with conventional methods of expressing this lipolytic enzyme. For example, in the present invention there is provided an enhanced/increased expression and/or an improved yield of the lipolytic enzyme compared with production of the lipolytic in another host organism (i.e. a host organism other than *T. reesei*). In particular, there is an increased expression and/or an improved yield of the lipolytic enzyme by the present invention (i.e. produced in the *Trichoderma reesei* cell) as compared with expression of the same lipolytic enzyme in an *Aspergillus tubingensis* cell (for example as taught in WO98/45453, as incorporated herein by reference).

A further advantage of the present invention is that the lipolytic enzyme produced in accordance with the present invention is easy to produce and isolate and/or purify and/or concentrate.

A further advantage of the present invention is that the lipolytic enzyme produced in accordance with the present invention is easy to re-solubilise.

A further advantage of the present invention is that the lipolytic enzyme produced in accordance with the present invention may be used as a granulate or as a solution.

Lipolytic Enzyme

The term "lipolytic enzyme" as used herein means an enzyme with triacylglycerol hydrolysing activity (classified as E.C. 3.1.1.3).

Suitably, the lipolytic enzyme of the present invention may exhibit one or more of the following additional activities: glycolipase activity (E.C. 3.1.1.26), phospholipase A2 activity (E.C. 3.1.1.4), phospholipase A1 activity (E.C. 3.1.1.32) or phospholipase B activity (E.C. 3.1.1.5). The term "glycolipase activity" as used herein encompasses "galactolipase activity".

Suitably, the lipolytic enzyme according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4) and/or phospholipase B activity (E.C. 3.1.1.5).

Isolated

In one aspect, preferably the lipolytic enzyme according to the present invention is in an isolated form. The term "isolated" means that the lipolytic enzyme is at least substantially free from at least one other component with which the lipolytic enzyme is naturally associated in nature and as found in nature. The term "isolated" may mean that the lipolytic enzyme is at least substantially free from at least one other component in the culture media in which it is produced. The lipolytic enzyme of the present invention may be provided in a form that is substantially free of one or more contaminants with which the substance might otherwise be associated or with which the enzyme may be produced in the *T. reesei* host. Thus, for example it may be substantially free of the cell(s) or one or more potentially contaminating polypeptides and/or nucleic acid molecules. The lipolytic enzyme may be isolated by separating the cell(s) from the broth during or after fermentation so that the lipolytic enzyme remains in the broth. The lipolytic enzyme may be isolated by subjecting the fermentation broth to cell separation by vacuum filtration.

Purified

In one aspect, preferably the lipolytic enzyme according to the present invention is in a purified form. The term "purified" means that the given component is present at a high level. The component is desirably the predominant component present in a composition. Preferably, it is present at a level of at least about 60%, or at least about 65%, or at least about 70%, or at least about 75%, or at least about 80% said level being determined on a dry weight/dry weight basis with respect to the total composition under consideration. For some embodiments the amount is at least about 85% said level being determined on a dry weight/dry weight basis with respect to the total composition under consideration.

Concentrate

In one aspect, preferably the lipolytic enzyme according to the present invention is used as a concentrate. The concentrate may be a concentrated form of the medium into which the enzyme has been excreted. Preferably, the concentrate may be a concentrated form of the medium into which the enzyme has been secreted and wherein the cell(s) have been removed.

Nucleotide Sequence

The scope of the present invention encompasses nucleotide sequences encoding proteins having the specific properties and/or parameters as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) Tetrahedron Letters 22, p 1859-1869, or the method described by Matthes et al., (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein encompassed in the present invention may be used in conjunction with other proteins, particularly enzymes. Thus the present invention also covers a combination of proteins wherein the combination comprises the protein/enzyme of the present invention and another protein/enzyme, which may be another protein/enzyme according to the present invention. This aspect is discussed in a later section.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 30, 35, 40, 45, 50, 55, 60, 65, 70, 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 30, 35, 40, 45, 50, 55, 60, 65, 70, 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI Advance™ 11 (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI Advance™ 11 package.

Alternatively, percentage homologies may be calculated using the multiple alignment feature in Vector NTI Advance™ 11 (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| | | | |
|---|---|---|---|
| FOR BLAST | | | |
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Variants/Homologues/Derivatives

The present invention also encompasses the use of variants, homologues and derivatives of any amino acid sequence of a protein or of any nucleotide sequence encoding such a protein.

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 30, 35, 40, 45, 50, 55, 60, 65, 70, 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 30, 35, 40, 45, 50, 55, 60, 65, 70, 75, 80, 85 or 90% identical, preferably at least 95, 96, 97, 98 or 99% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software than can perform sequence comparisons include, but are not limited to, the BLAST package (see Ausubel et al., 1999 Short Protocols in Molecular Biology, 4th Ed-Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-amino butyric acid*, L-amino butyric acid*, L-amino isobutyric acid*, L-amino caproic acid#, 7-amino heptanoic acid*, L-methionine sulfone*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or -alanine residues. A further form of variation, involves the presence of one or more amino acid residues in peptoid form, will be well understood by those skilled in the art. For the avoidance of doubt, "the peptoid form" is used to refer to variant amino acid residues wherein the -carbon substituent group is on the residue's nitrogen atom rather than the -carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na3citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na3citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Molecular Evolution

As a non-limiting example, it is possible to produce numerous site directed or random mutations into a nucleotide sequence, either in vivo or in vitro, and to subsequently screen for improved functionality of the encoded polypeptide by various means.

In addition, mutations or natural variants of a polynucleotide sequence can be recombined with either the wildtype or other mutations or natural variants to produce new variants. Such new variants can also be screened for improved functionality of the encoded polypeptide. The production of new preferred variants can be achieved by various methods well established in the art, for example the Error Threshold Mutagenesis (WO 92/18645), oligonucleotide mediated random mutagenesis (U.S. Pat. No. 5,723,323), DNA shuffling (U.S. Pat. No. 5,605,793), exo-mediated gene assembly WO00/58517. The application of these and similar random directed molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following:

optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate Site-Directed Mutagenesis Once a protein-encoding nucleotide sequence has been isolated, or a putative protein-encoding nucleotide sequence has been identified, it may be desirable to mutate the sequence in order to prepare a protein of the present invention.

Mutations may be introduced using synthetic oligonucleotides. These oligonucleotides contain nucleotide sequences flanking the desired mutation sites.

A suitable method is disclosed in Morinaga et al., (Biotechnology (1984) 2, p646-649). Another method of introducing mutations into enzyme-encoding nucleotide sequences is described in Nelson and Long (Analytical Biochemistry (1989), 180, p 147-151).

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, Molecular Cloning: A Laboratory Manual, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms *T. reesei*.

Expression of Enzymes

The nucleotide sequence for use in the present invention may be incorporated into a recombinant replicable vector.

The vector may be used to replicate and express the nucleotide sequence, in protein form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

In one embodiment a suitable promoter may be a cellobiohydrolase promoter.

In one embodiment a suitable promoter may be a cellobiohydrolase promoter obtainable (or obtained) from *T. reesei*.

The promoter can additionally include features to ensure or to increase expression in a suitable host. For example, the features can be conserved regions such as transcription factor binding sites or deleted repressor binding sites.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any *T. reesei* cell that comprises either the nucleotide sequence or an expression vector as described above and which is used in the recombinant production of a protein having the specific properties as defined herein.

Thus, a further embodiment of the present invention provides *T. reesei* host cells transformed or transfected with a nucleotide sequence that expresses the protein of the present invention.

The use of a *T. reesei* host cell may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes *T. reesei* that comprises the nucleotide sequence coding for the polypeptide according to the present invention and/or products obtained therefrom, and/or wherein a promoter can allow expression of the nucleotide sequence according to the present invention when present in the organism.

A suitable organism is *T. reesei*.

The term "transgenic organism" in relation to the present invention includes a *T. reesei* that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

Transformation of Host Cells/Organism

Filamentous fungi cells may be transformed using various methods known in the art—such as a process involving protoplast formation and transformation of the protoplasts followed by regeneration of the cell wall in a manner known.

General teachings on the transformation of fungi are presented in following sections.

Transformed Fungus

The host organism is *T. reesei* and the like.

Transforming filamentous fungi is discussed in U.S. Pat. No. 5,741,665 which states that standard techniques for transformation of filamentous fungi and culturing the fungi are well known in the art. An extensive review of techniques as applied to *N. crassa* is found, for example in Davis and de Serres, Methods Enzymol (1971) 17A: 79-143.

Further teachings which may also be utilised in transforming filamentous fungi are reviewed in U.S. Pat. No. 5,674,707.

In addition, gene expression in filamentous fungi is taught in Punt et al. (2002) Trends Biotechnol 2002 May; 20(5):200-6, Archer & Peberdy Crit Rev Biotechnol (1997) 17(4):273-306.

The present invention encompasses the production of transgenic filamentous fungi according to the present invention prepared by use of these standard techniques.

Culturing and Production

*T. reesei* host cells transformed with the nucleotide sequence of the present invention may be cultured under conditions conducive to the production of the encoded polypeptide and which facilitate recovery of the polypeptide from the cell(s) and/or culture medium.

In one embodiment the transformed or transfected *T. reesei* cell(s) provided in accordance with the present invention is cultured under selective conditions to allow for selection of the cell(s) transformed or transfected with the lipolytic enzyme as defined herein.

The medium used to cultivate the cell(s) may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the -amylase gene (*Bacillus*).

In one embodiment preferably the signal peptide is that shown in SEQ ID NO: 1 as bold in FIG. 15. In one embodiment the signal peptide shown in bold in FIG. 15 is cleaved off post-translationally to provide a peptide having the sequence shown in SEQ ID NO: 2.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

The amino acid sequence for use according to the present invention may be produced as a fusion protein, for example to aid in extraction and purification. Examples of fusion protein partners include glutathione-S-transferase (GST), 6×His, GAL4 (DNA binding and/or transcriptional activation domains) and (-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Additional POIs

The sequences for use according to the present invention may also be used in conjunction with one or more additional proteins of interest (POIs) or nucleotide sequences of interest (NOIs).

Non-limiting examples of POIs include: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, -galactosidases, -galactosidases, -glucanases, glucan lyases, endo-glucanases, glucoamylases, glucose oxidases, -glucosidases, -glucosidases, glucuronidases, hemicellulases, hexose oxidases, hydrolases, invertases, isomerases, laccases, phospholipases, galactolipases, lipid acyltransferase, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: O2-oxidoreductase, EC 1.1.3.5) or combinations thereof. The NOI may even be an antisense sequence for any of those sequences.

The POI may even be a fusion protein, for example to aid in extraction and purification.

The POI may even be fused to a secretion sequence.

Other sequences can also facilitate secretion or increase the yield of secreted POI. Such sequences could code for chaperone proteins as for example the product of *Aspergillus niger* cyp B gene described in UK patent application 9821198.0.

The NOI may be engineered in order to alter their activity for a number of reasons, including but not limited to, alterations which modify the processing and/or expression of the expression product thereof. By way of further example, the NOI may also be modified to optimise expression in a particular host cell. Other sequence changes may be desired in order to introduce restriction enzyme recognition sites.

The NOI may include within it synthetic or modified nucleotides—such as methylphosphonate and phosphorothioate backbones.

The NOI may be modified to increase intracellular stability and half-life. Possible modifications include, but are not limited to, the addition of flanking sequences of the 5' and/or 3' ends of the molecule or the use of phosphorothioate or 2'O-methyl rather than phosphodiesterase linkages within the backbone of the molecule.

Large Scale Production/Application

In one preferred embodiment of the present invention, the lipolytic enzyme is used for large scale applications and/or is produced on a large scale.

The term large scale means in a fermentor or culturing conditions of at least 1000 liters.

Preferably the lipolytic enzyme is produced in a quantity of at least 5 g per liter of the total cell culture volume after cultivation of the host organism. Preferably, the lipolytic enzyme is produced in a quantity of at least 10 g per liter of the total cell culture volume after cultivation of the host organism. Preferably, the lipolytic enzyme is produced in a quantity of at least 15 g per liter of the total cell culture volume after cultivation of the host organism. Preferably, the lipolytic enzyme is produced in a quantity of at least 20 g per liter of the total cell culture volume after cultivation of the host organism.

Fermentation

The enzymes of the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulphur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, ~volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Trichoderma reesei* the temperature generally will be within the range of about 20° C. to 40° C., generally preferably in the range of about 25° C. to 34° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 24 to 500 hours, preferably presently about 24 to 400 hours. Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps. As described above, the time to reach this level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is much to be preferred for ease of control, production of uniform quantities of products, and most economical uses of all equipment. If desired, part or all of the carbon and energy source material and/or part of the assimilable nitrogen source such as ammonia can be added to the aqueous mineral medium prior to feeding the aqueous mineral medium to the fermentor. Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15 L Biolafitte (Saint-Germain-en-Laye, France).

The collection and purification of the enzymes of the present invention from the fermentation broth can also be done by procedures known per se in the art. The fermentation broth will generally contain cellular debris, including cells, various suspended solids and other biomass contaminants, as well as the desired enzyme product of the present invention, which are preferably removed from the fermentation broth by means known in the art. Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate using techniques such as ultrafiltration, evaporation or precipitation. Precipitating the proteinaceous components of the supernatant or filtrate may be accomplished by means of a salt, e.g., ammonium sulfate. Further purification may optionally be achieved by crystallization or by a variety of chromatographic procedures, e.g., ion exchange chromatography, affinity chromatography or similar art recognized procedures.

The lipase can be further formulated before use in foodstuffs. The lipase can be in a liquid formulation, dried or granulated.

In one embodiment a carrier can be used, preferably the carrier is wheat or a wheat component.

In one embodiment the lipase is dried on wheat or dried on one or more wheat components.

In one embodiment the lipase is in a liquid formulation suitable for consumption, preferably such liquid composition contains either buffer, salts, sorbitol and/or glycerol.

In one embodiment the lipase is granulated or co-granulated with other enzymes.

Food

The enzyme of the present invention may be used as—or in the preparation of—a food. Here, the term "food" means food intended for human consumption. Also, the term "foodstuff" means a foodstuff intended for human consumption.

The food may be in the form of a solution or as a solid—depending on the use and/or the mode of application and/or the mode of administration.

When used as, or in the preparation of, a food—such as functional food—the enzyme of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

Food Ingredient

The enzyme of the present invention may be used as a food ingredient and/or may be comprised in a food additive composition for humans.

As used herein the term "food ingredient" includes a formulation which is or can be added to functional foods or foodstuffs as a nutritional supplement and/or fiber supplement.

The food ingredient may be in the form of a solution or as a solid—depending on the use and/or the mode of application and/or the mode of administration.

Food Supplements

The composition of the present invention may be—or may be added to—food supplements for humans.

Functional Foods

The composition of the present invention may be—or may be added to—functional foods for humans.

As used herein, the term "functional food" means food which is capable of providing not only a nutritional effect and/or a taste satisfaction to a human, but is also capable of delivering a further beneficial effect to the consumer.

Accordingly, functional foods are ordinary foods that have components or ingredients (such as those described herein) incorporated into them that impart to the food a specific functional—e.g. medical or physiological benefit—other than a purely nutritional effect to a human.

Although there is no legal definition of a functional food, most of the parties with an interest in this area agree that they are foods marketed as having specific health effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

Food Products

The composition of the present invention can be used in the preparation of food products for humans such as one or more of: jams, marmalades, jellies, dairy products (such as milk or cheese), meat products, poultry products, fish products and bakery products.

By way of example, the enzyme of the present invention can be used as ingredients to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, breakfast cereals, instant noodles and cup noodles, instant soups and cup soups, balanced foods and drinks, sweeteners, tacos, tortillas, texture improved snack bars, fibre bars, bake stable fruit fillings, care glaze, chocolate bakery filling, cheese cake flavoured filling, fruit flavoured cake filling, cake and doughnut icing, heat stable bakery filling, instant bakery filling creams, filing for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

A enzyme according to the present invention can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat & lite natural cheddar cheese, low fat Swiss style yoghurt, aerated frozen desserts, and novelty bars, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the foodstuff is a beverage.

For certain aspects, preferably the foodstuff is a bakery product—such as bread, Danish pastry, biscuits or cookies.

Feed

The enzyme of the present invention may be used as—or in the preparation of—an animal feed or a component thereof. Thus, the present invention also encompasses a feed comprising or made from the enzyme of the present invention, and a process for making same.

Detergent

The enzyme of the present invention may be used as—or in the preparation of—a detergent or a component thereof. Thus, the present invention also encompasses a detergent comprising or made from the enzyme of the present invention, and a process for making same.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Lab oratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

The invention will now be described, by way of example only, with reference to the Figures and the following Examples.

Example 1

Expression of the *Aspergillus tubingensis* Lipase 3 in *Trichoderma reesei*

Figure 3:
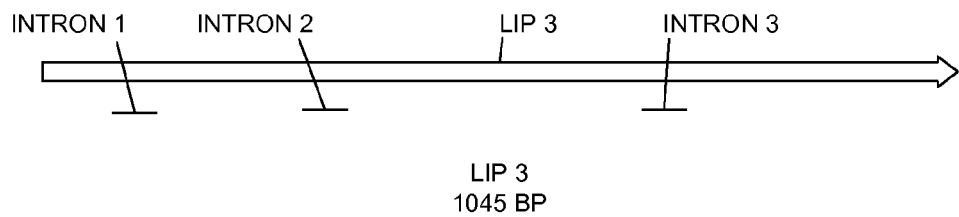
FIG. 3 shows a schematic diagram of the *Aspergillus tubingensis* lipolytic enzyme genomic DNA.
Figure 4:
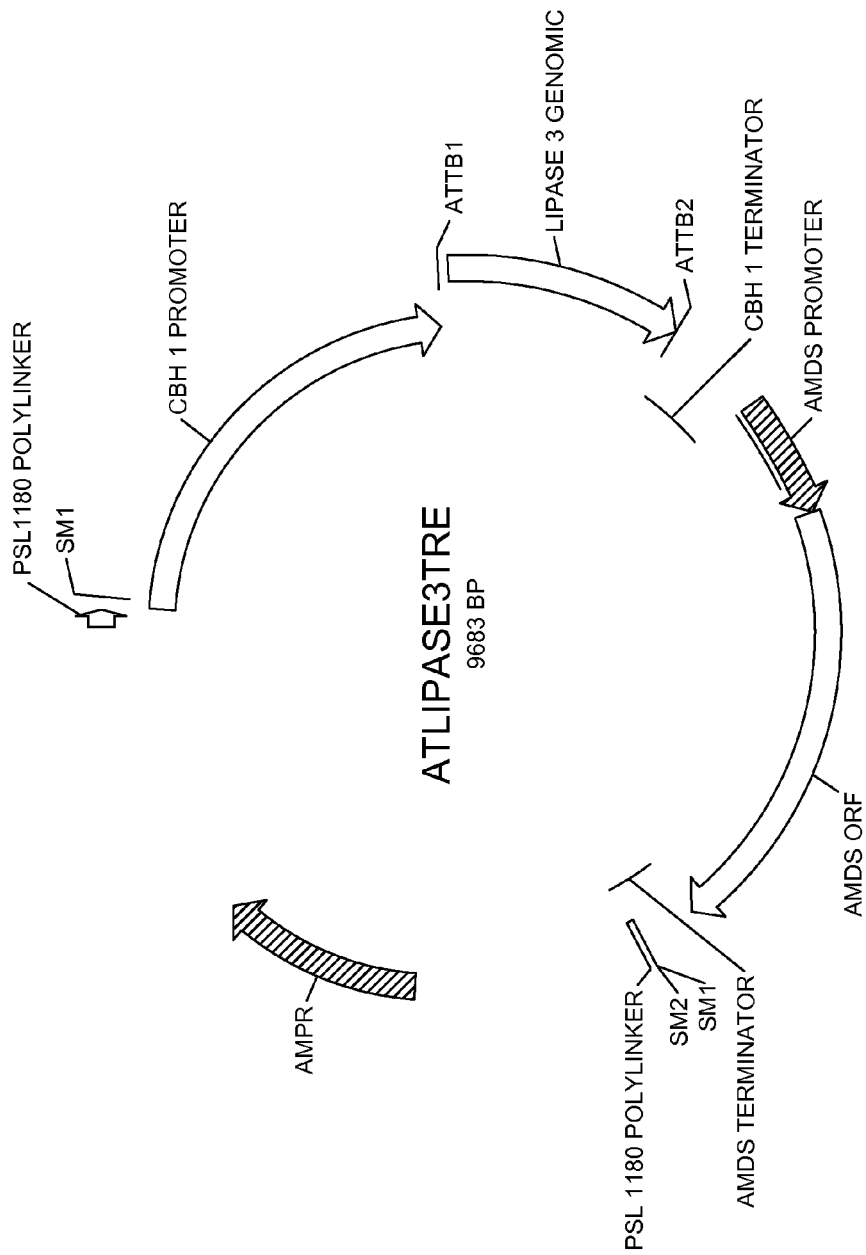
FIG. 4 shows the expression construct "ATlipase3Trex".

1. Expression Construct & Strain used for Transformation pDONR™221 plasmid DNA obtained from Invitrogen (catalogue no. 12536-017) was used as the donor vector. pDONR221::lip 3 containing the *Aspergillus tubingensis* lipase 3 genomic DNA (FIG. 3) was recombined into the *T. reesei* gateway destination vector pTrex3G (described in detail in WO 05/001036), resulting in the final expression construct ATlipase3Trex (FIG. 4).

The expression cassette contained the promoter and terminator regions of the *T. reesei* cellobiohydrolase 1 (cbh1) gene. It also contained the *Aspergillus nidulans* acetamidase, amdS gene as a selectable marker for transformation of *T. reesei*.

The *Aspergillus tubingensis* lipase 3 genomic DNA encodes a lipase 3 lipolytic enzyme having the amino acid sequence shown in SEQ ID No. 1.

The term "lipase 3" when used herein refers to a lipolytic enzyme comprising the amino acid sequence shown in SEQ ID No. 2, such as the amino acid sequence shown in SEQ ID No. 1. Seq. ID No. 1 contains the signal seq and seq. ID No. 2 is the mature lipase protein without the signal sequence.

The strain used for transformation was *Trichoderma reesei*, a derivative of the non-GMM strain RL-P37 from which the genes encoding the two secreted cellobiohydrolases, CBHI and CBHII, and two of the secreted endoglucanases, EGI and EGII, have been deleted.

The Expression Vector pTrex3 g.

The following describes the construction of the vector pTrex3 g which may be used to express the genes of the present invention.

This vector is based on the *E. coli* vector pSL1180 (Pharmacia Inc., Piscataway, N.J., USA) which is a pUC118 phagemid based vector (Brosius, J. (1989) DNA 8:759) with an extended multiple cloning site containing 64 hexamer restriction enzyme recognition sequences. It was designed as a Gateway destination vector (Hartley, J. L., Temple, G. F. and Brasch, M. A. (2000) Genome Research 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selectable marker in transformation of *T. reesei*.

The details of pTrex3 g are as follows. The vector is 10.3 kb in size.

Inserted into the polylinker region of pSL1180 are the following segments of DNA:

1. A 2.2 bp segment of DNA from the promoter region of the *T reesei* cbh1 gene
2. The 1.7 kb Gateway reading frame A cassette acquired from Invitrogen that includes the attR1 and attR2 recombination sites at either end flanking the chloramphenicol resistance gene (CmR) and the ccdB gene
3. A 336 bp segment of DNA from the terminator region of the *T. reesei* cbh1 gene
4. A 2.7 kb fragment of DNA containing the *Aspergillus nidulans* amdS gene with its native promoter and terminator regions.

2. Transformation of *T. reesei* Quad Delete Host Strain

The expression construct, ATlipase3Trex, containing the *A. tubingensis* lipase 3 gene was transformed into a *T. reesei* strain using electroporation or biolistic transformation by particle bombardment using the PDS-1000 Helium system (BioRad Cat. No. 165-02257). PCR products containing only fungal DNA or the entire expression plasmid were used for generating transformants by biolistic transformation and electroporation.

A. Transformation by Electroporation

The *T. reesei* host strain to be transformed was grown to full sporulation on PDA plates for 5 days. Spores from 2 plates were harvested with 1.2M sorbitol and filtered through miracloth to get rid of the agar. Spores were transferred to a 50 ml falcon tube and washed by repeated centrifugation 5-6 times with 50 ml water. The spores were resuspended in a small volume (less than 2× pellet volume) using 1.2M sorbitol solution. The spore suspension was then kept on ice. 90 ul of spore suspension was aliqouted into the electroporation cuvette (E-shot, 0.1 cm standard electroporation cuvette from Invitrogen). 10-20 ul DNA construct (plasmid FIG. 4 or PCR product) were added to the spore suspension and electroporation was set at 16 kV/cm, 25 µF, 50Ω. After electroporation, the spore suspension was left on ice, resuspended in 5 parts 1.0M sorbitol and 1 part YEPD, and allowed to germinate by incubation at 28 C with shaking 250 rpm overnight. The next day, the germlings were plated in agar plates containing acetamide. Transformants were picked and transferred individually to acetamide agar plates.

B. Transformation by Particle Bombardment (Biolistic Transformation)

A suspension of spores from a quad deleted strain of *T. reesei* was prepared. 200 ul of spore suspension was spread onto the center of the minimal medium (MM) acetamide plates. (MM acetamide plates had the following composition: 0.6 g/l acetamide; 1.68 g/l CsCl; 20 g/l glucose; 20 g/l KH2PO4, 0.6 g/l CaCl2 2H20; 1 ml/l 1000× trace elements solution; 20 g/l Noble agar, and pH5.5. 1000× trace elements solution contained 5.0 g/l FeSO4 7H2O; 1.6 g/l MnSO4; 1.4 g/l ZnSO4 7H2O and 1.0 g/l CoCl2 6H2O. The spore suspension was allowed to dry on the surface of MM acetamide medium for 1 hour in the sterile hood. Transformation followed the manufacturer's instruction. 60 mg of tungsten particles were placed in a microfuge tube. 1 ml of ethanol was added and allowed to stand for 15 seconds. The ethanol was removed and the particles were washed three times with sterile dH₂O before 250 ul of 50% (v/v) sterile glycerol was added. 25 ul of tungsten particle suspension was placed onto a microfuge tube. While continuously vortexing, the following were added: 5 ul (100-200 ng/ul) of plasmid DNA, 25 ul of 2.5M CaCl2 and 10 ul of 0.1M spermidine. The particles were centrifuged for 3 seconds. The supernatant was removed and the particles were washed with 200 ul of 100% ethanol and centrifuged for 3 seconds. The supernatant was removed. 24 ul 100% ethanol was added and mixed by pipetting, then 8 ul aliquots of particles were removed and placed in the centre of microcarrier disks that were held in a desiccator. Once the tungsten/DNA solution had dried the microcarrier disk was placed in the bombardment chamber along with the plate of MM acetamide with spores and the bombardment process was carried out according to the manufacturer's instructions. After bombardment of the plated spores with the tungsten DNA particles, the plates were incubated at 28 C. Transformed colonies were transferred to fresh plates of MM acetamide medium and incubated at 28 C.

3. Growth of Transformants in Microtiter Plates

After 5 days of growth on MM acetamide plates, transformants obtained by electroporation or by biolistic transformation and displaying stable morphology were inoculated into 200 ul Defined medium with glucose/sophorose in a 96-well microtiter plates. Defined medium with glucose/sophorose (per liter) consists of $NH_42 SO_4$ 5 g, PIPPS buffer 33 g, Casamino Acids 9 g, $KH_2PO_4$ 4.5 g, $CaCl_2$ (Anhydrous) 1 g, $MgSO_4.7H_2O$ 1 g, pH to 5.50 adjusted with 50% NaOH with milli-Q $H_2O$ bring to 966.5 mL. After sterilization, the following were added: Mazu 5 mL, Glucose/Sophrose 60% 26 mL and 400×*T. reesei* Trace Metals 2.5 mL. The microtiter plate was incubated in an oxygen growth chamber at 28° C. for 5 days.

Example 2

Screening by Lipase Spot Assay & SDS-PAGE

Figure 5:
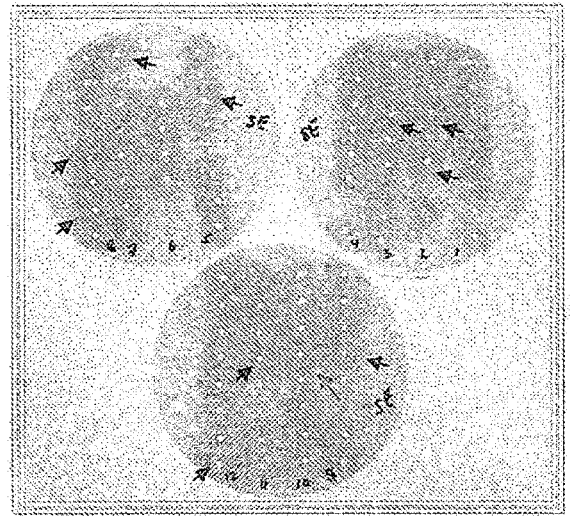
FIG. 5 shows results of a Lipase Activity Assay performed on supernatant from *Trichoderma reesei* transformants.

Mycelium was removed by centrifugation and the supernatant was analysed for lipase activity using the spot assay. Lipase plate assay is based on the release of fatty acid from the substrate (tributyrin) in the presence of lipase. A pink colour is formed when fatty acid is released and forms a complex with Rhodamine B. The assay plate contained 2.0 g Bacto Agar (dissolved by heating for 5 minutes in 100 ml 50 mM Sodium phosphate buffer pH 5.5. The solution was kept at 70° C. water bath and while stirring, 0.5 ml 2% Rhodamine and 40 ml tributyrin was added. The mixture was subjected to sonication for 2 minutes and 10-15 ml was poured into petri dishes. Holes were punched and the culture supernatant was applied on to the holes. The plates were incubated at 37° C. until a pink colour was formed indicating the presence of lipolytic activity. Supernatant (10 ul) from transformants was checked for lipase activity using the spot assay as shown in FIG. 5, arrows indicate the appearance of the pink colour after 30 minutes of incubation at 37° C., showing high lipase activity.

Figure 6:
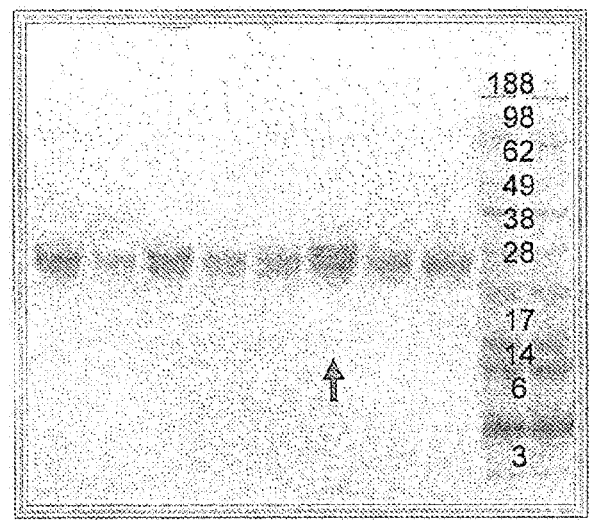
FIG. 6 shows a protein profile by SDS-PAGE performed on supernatant from *Trichoderma reesei* transformants. The lane indicated with an arrow shows one of the transformants that expresses very high levels of the lipolytic enzyme ("lipase 3").
Figure 7:
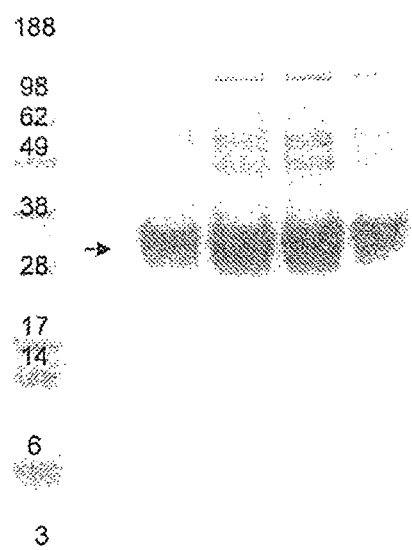
FIG. 7 shows a protein profile by SDS-PAGE of supernatant from *Trichoderma reesei* transformants cultivated in a 3 liter fermentor. The arrow indicates the lipolytic enzyme ("lipase 3") protein band.

The protein profile of those transformants exhibiting high lipase activity was determined by SDS-PAGE using NuPAGE 4-12% polyacrylamide gels and MES as running buffer. Samples of the supernatant were mixed with appropriate volume of 2× sample loading buffer with reducing agent. The gels were stained with Simply blue Safestain (Invitrogen). In FIG. 6 the lane marked with an arrow shows one of the transformants expressing very high levels of lipase 3 appearing as a double band. The rest of the transformants showed distinct and slightly fuzzy single bands. The best transformant grown in 3 liter fermentor gave a total secreted protein titer of at least 20 g/liter and SDS-PAGE analysis showed a broad lipase band (FIG. 7).

Example 3

Large Scale Fermentation (14-Liters) of Lipase 3 Transformants

*Trichoderma reesei* transformants were cultured in fermenters as described in WO 2004/035070. Four different transformants, generated by electroporation, were cultured. Measurement of total protein and lipase activity in culture supernatants, after cell removal, indicated that in excess of 20 grams per liter lipase was present after 160 hours of fermentation. Two strains, generated by biolistic transformation, were also grown. These showed in excess of 20 grams per liter lipase in the culture supernatant after 160 hours of fermentation. The amount of lipase 3 produced by these transformants was far in excess of the amount of lipase 3 produced by other microbial host species (FIG. 8)

*Trichoderma reesei* transformants were cultured in fermentors. Four different transformants, generated by electroporation, were cultured. Measurement of total protein and lipase activity in culture supernatants, after cell removal, indicated that in excess of 20 grams per liter lipase was present after 160 hours of fermentation. Two strains, generated by biolistic transformation, were also grown. These showed in excess of 20 grams per liter lipase in the culture supernatant after 160 hours of fermentation. The amount of lipase 3 produced by these transformants was far in excess of the amount of lipase 3 produced by other microbial host species (FIG. 8).

Example 4

Solubility of Lipase 3

Figure 11A:
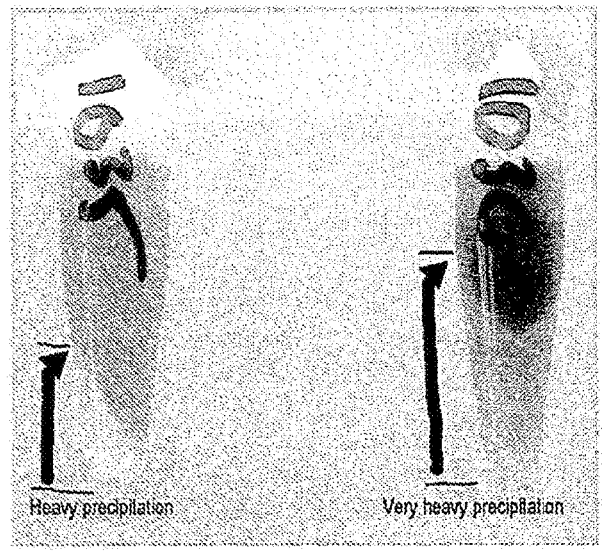
FIG. 11a shows two different UFCs (ultra-filtration concentrates) showing precipitation of the lipolytic enzyme "lipase 3". Less concentrated protein in 1035 UFC shows heavy precipitation and more concentrated protein in 1036 UFC shows very heavy precipitation. Precipitation is concentration dependent—the higher the protein concentration the more likely it is to precipitate.

Surprisingly the present inventors have found that *Trichoderma reesei* is capable of producing lipase 3 at very high levels. Down stream processing of the lipase after fermentation requires concentration of the culture broth 4× by ultrafiltration using a membrane with a 10,000 molecular weight cut-off. Lipase 3 is prone to precipitation as shown in FIG. 11a. Heavy precipitation is observed in the more concentrated UFC. The presence of lipase 3 protein in the precipitates was confirmed by SDS-PAGE.

Figure 11B:
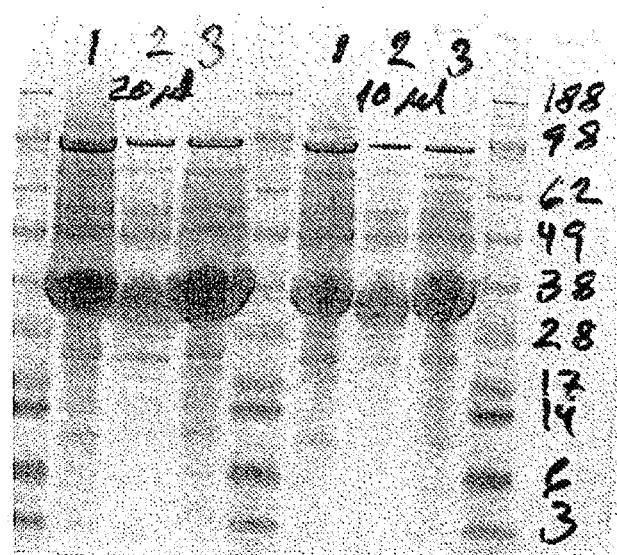
FIG. 11b shows an SDS-PAGE showing the presence of the lipolytic enzyme "lipase 3" protein in the precipitates of FIG. 11a:
Lane 1—Centrifuged filtered crude supernatant
Lane 2—Resolubilized pellet from UFC 1035
Lane 3—Resolubilized pellet from UFC 1036.

FIGS. 11a and 11b show that precipitation of lipase 3 is concentration dependent.

FIG. 11a shows two different ultra-filtration concentrates (UFCs) showing precipitation of lipase 3. 1035 UFC contains less concentrated protein and shows heavy precipitation. 1036 UFC contains more concentrated protein and shows very heavy precipitation.

FIG. 11b shows an SDS-PAGE showing the presence of lipase 3 protein in the precipitates shown in FIG. 11a:

Lane 1 Centrifuged filtered crude supernatant
Lane 2 Resolubilized pellet from UFC 1035
Lane 3 Resolubilized pellet from UFC 1036

For resolubilisation of lipase precipitates, stock buffer was used. Stock buffer consists of 1.0 M Na-Phosphate buffer, pH 8.0 $Na_2HPO_4.2H_2O$ (177.99 g) added to 900 ml of DI water. To 10.0 g samples of the crude lipase 3 UFC 1036, pH 4.44 was added 50, 100, 200, 400, and 500 µl of buffer stock solution to a final concentration of 5, 10, 20, 40, and 50 mM Na-Phosphate respectively. All the vials were mixed and left at room temperature for a few minutes.

Figure 12:
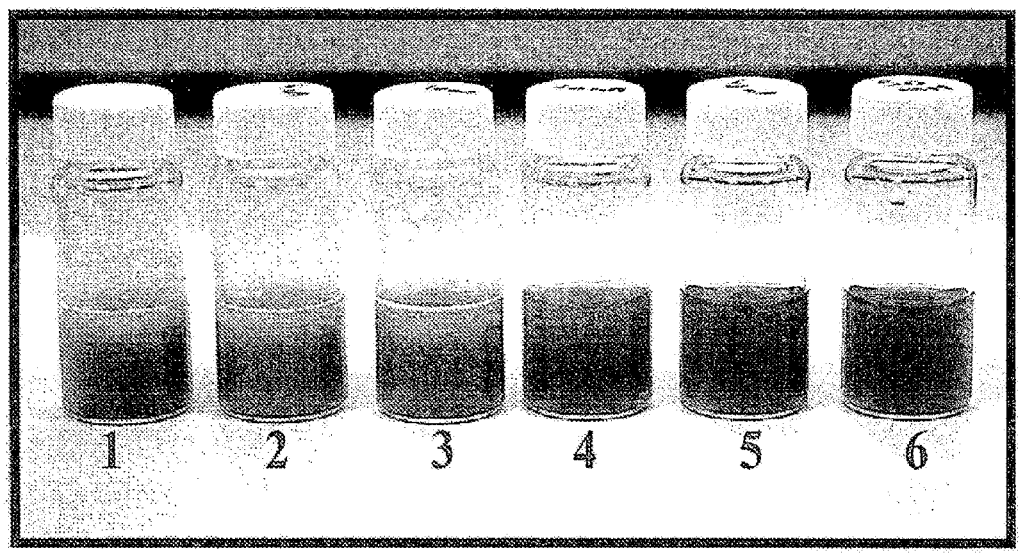
FIG. 12 shows resolubilisation of precipitated lipolytic enzyme ("lipase 3") using different concentrations of sodium phosphate buffer. Samples were at pH 5.30.
Lane 1. Crude, control.
Lanes 2-6: 5 mM, 10 mM, 20 mM, 40 mM & 50 mM sodium phosphate.

As shown in FIG. 12, the addition of Na-phosphate above 40 mM brought the precipitated lipase 3 into solution. The resulting solution was clear and free from any solid matter. The pH of the samples was measured at pH 5.3 (at 50 mM Na—P concentration).

Example 5

Characterization of Recombinant Lipase 3 by MALDI-TOF/MS Analysis & Proteolytic Digestion Lipase 3 expressed by *T. reesi* was purified from the culture supernatant using a combination of ion exchange and hydrophobic interaction chromatography. Deglycosylation was carried out using endoglycosidase H in reaction buffer consisting of 50 mM Sodium Citrate, pH 5.5. Endoglycosidase H (2.0 mg/mL), was added to lipase 3 at a protein ratio from 1/1000 to 1/100 (w/w). The deglycosylation reaction was performed at 37° C. for 3 hours. The reacted protein sample was put on a ZipTip® (Micro $C_4$ reversed-phase column) (Millipore, Bedford, Mass.) for sample cleanup prior to the MALDI-TOF/MS analysis. The cleanup process was performed to desalt the samples. At least five cycles of wash solution consisting of 5% methanol in 0.1% TFA/water wash was used. Afterwards the samples were eluted for mass spectrometry.

MALDI-TOF/MS Analysis of Intact Protein

The desalted protein sample was prepared for MALDI-TOF/MS analysis by co-crystallizing an equal volume (1 μL) of sample with Sinapinic acid matrix (saturated in 50% acetonitrile, 0.1% formic acid) using the dried droplet method. Protein mass spectra were obtained using a Voyager D E-STR MALDI-TOF mass spectrometer (Applied Biosystems, Foster City, Calif., USA). The MS instrument settings were as follows for the 20000-80000 m/z range: linear mode of operation, delayed extraction mode, positive polarity, 25 kV acceleration voltage, 93% grid voltage, and 750 nsec extraction delay time. 300-laser shots/spectrum and BSA was used as external calibrant.

Proteolytic Digestion & N-glycosylation site(s) Mapping by LC/MS/MS Analysis

All Endo-H treated liquid samples were precipitated with 10% TCA followed by the reduction reactions with 20 mM DTT @ 50° C. for 15-20 min. The alkylation reaction was also performed with 55 mM iodoacetamide. The alkylation reaction was allowed to proceed in the dark for 45 min at room temp. Proteolytic digestions were performed by incubation with various proteases in 25 mM ammonium bicarbonate for 4 hr at 37° C. (enzyme to substrate ratio was 1:20). Peptide mapping carried out using 3 different proteolytic digestions (trypsin, chymotrypsin, Endoproteinase GluC) on the glycosylated lipase confirmed the absence of protein modification by truncation and the presence of an intact lipase protein with authentic N- and C-terminal ends.

Lipase 3 has 2 potential N-glycosylation sites at N32 and N242. Peptide mapping was carried out for both lipase 3 (untreated) and Endo-H treated. To determine the site of N-glycosylation, MS and MS/MS data were acquired using the Surveyor™ LC system coupled to the LCQ Advantage or LCQ Deca XP (ThermoFinnigan, San Jose, Calif.). The HPLC gradient was programmed from 0% to 70% B over 50 minutes. Solvent A: 0.1% TFA in water and Solvent B: 0.08% TFA in acetonitrile. Data Processing was performed using TurboSEQUEST and Xcalibur (ThermoFinnigan, San Jose, Calif.).

Figure 13:
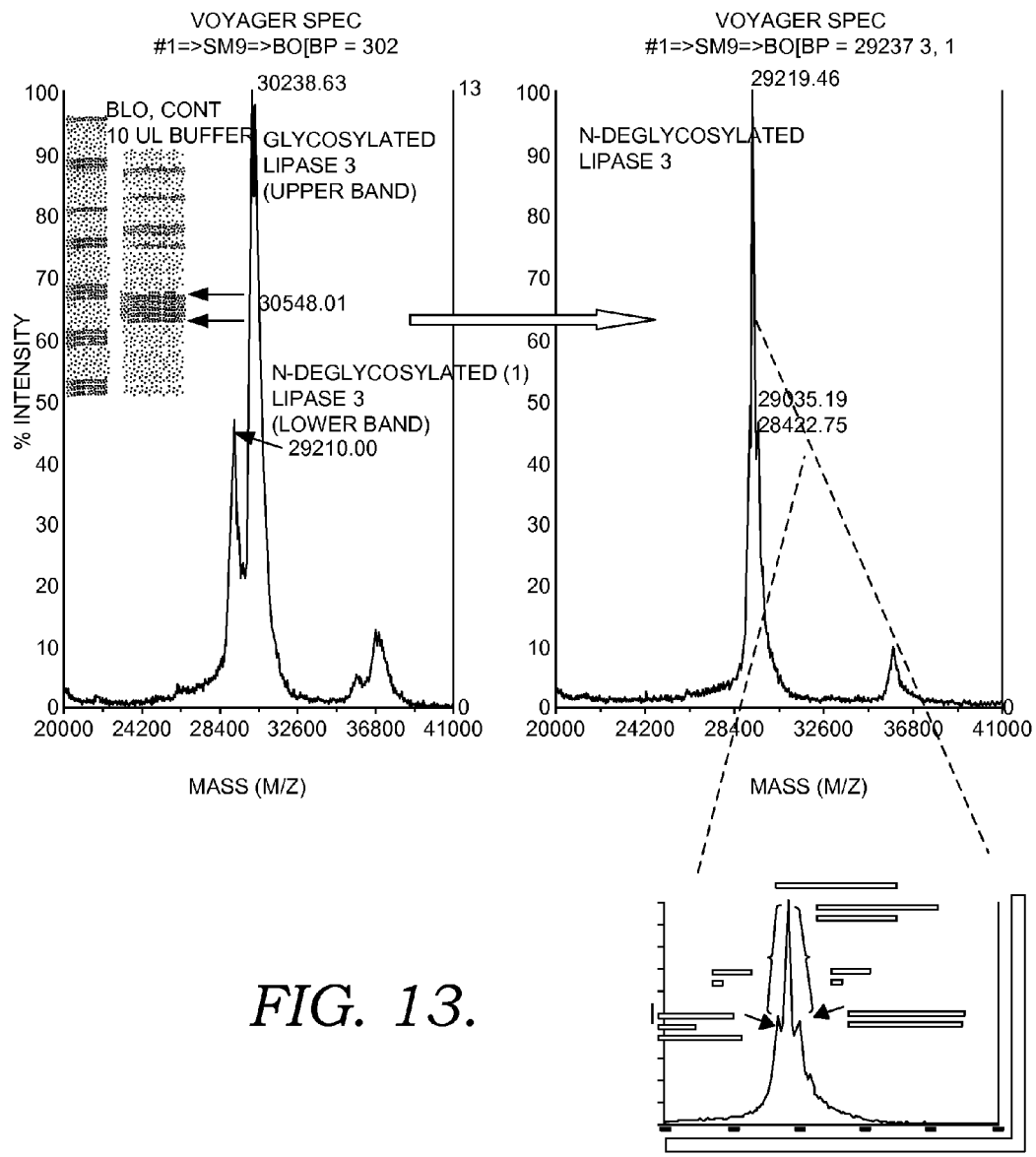
FIG. 13 shows characterization of recombinant lipolytic enzyme "lipase 3" by MALDI-TOF/MS analysis of glycosylated compared with de-glycosylated lipase. The size of N-glycan is about 1384 Da and the lipolytic enzyme (lipase 3) molecules may have glycans attached at N32 site (when considering SEQ ID No. 2)

As shown in FIG. 13, SDS-PAGE showed the recombinant lipase secreted by *Trichoderma* appeared as a double band prior to endoglycosidase H treatment. MALDI-TOF/MS analysis showed that the higher molecular weight species was a glycosylated form of lipase 3 with a molecular weight of 30,236 Dalton and the lower molecular weight species was a de-glycosylated form with molecular weight of 29,210 Dalton. Experimentally deglycosylated lipase samples were generated using endoglycosidase H. The molecular weights observed after endoglycosidase H treatment were 29,035 Dalton (presumed to be a non-glycosylated form), 29,219 (presumed to be a form of lipase 3 with 1 N-linked N-acetylglucosamine at position N32 or N242) and 29,422 (presumed to be a form of lipase 3 with 2 N-aceyltglucosamine residues attached to the protein backbone at positions N32 and N242). The glycan chain that is present prior to de-glycosylation with endoglycosidase H has a molecular weight of approximately 1384 daltons with the majority of lipase molecules having glycan attached only to the N32 site (numbered in accordance with SEQ ID No. 2).

Example 6

Specific Activity of the Lipolytic Enzyme Lipase 3 Produced in *T. reesei* Using 2 Different Substrates The purified lipase 3 was subjected to deglycosylation by treatment with endoglycosidase H. The untreated and the deglycosylated samples were characterised by measurement of specific activities using both short chain (C4) and long chain (C18) substrates.

Figure 14:
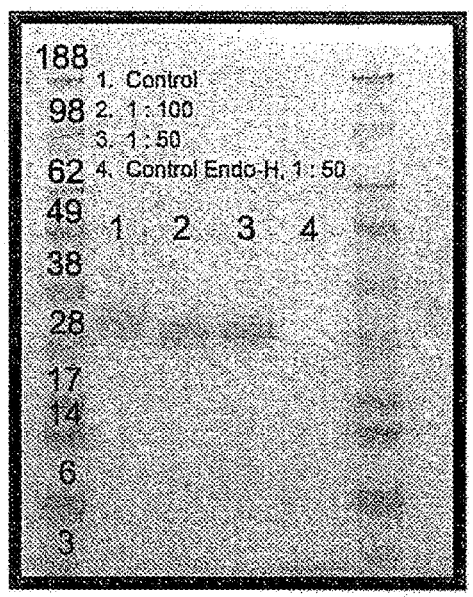
FIG. 14 shows an SDS-PAGE protein analysis of purified lipolytic enzyme (lipase 3) subjected to deglycosylation. Deglycosylation enzyme: Endo-H, 2.0 mg/ml. Endo-H was added at a ratio of 1:50 and 1:100 (w/w) and incubated for 20 hours at room temperature, pH 5.5.
Lane 1—Control
Lane 2—1:100 dilution of supernatant
Lane 3—1:50 dilution of supernatant The specific activities are shown in table 1 below. N-linked glycosylation has no effect on the specific activity of lipolytic enzyme (lipase 3) protein. Deglycosylating the lipolytic enzyme (lipase 3) did not affect enzyme activity.

As shown in FIG. 14 and Table 2 the presence of glycan side chains has no effect on the specific activity of the protein.

Table 2 shows the results of the deglycosylation experiments. The sample was Purified *Trichoderma* lipase 3 and the deglycosylation enzyme was Endo-H.

| | Specific activity, % | |
|---|---|---|
| Sample | LIPU/ml (Short chain, C4) | LUSol/ml (Long chain, C18) |
| Control (lane 1) | 100 | 100 |
| 1:100 Endo-H (lane 2) | 99.4 | 103 |
| 1:50 Endo-H (lane 3) | 97.7 | 105 |

Example 7

Southern Blot Analysis

Figure 9:
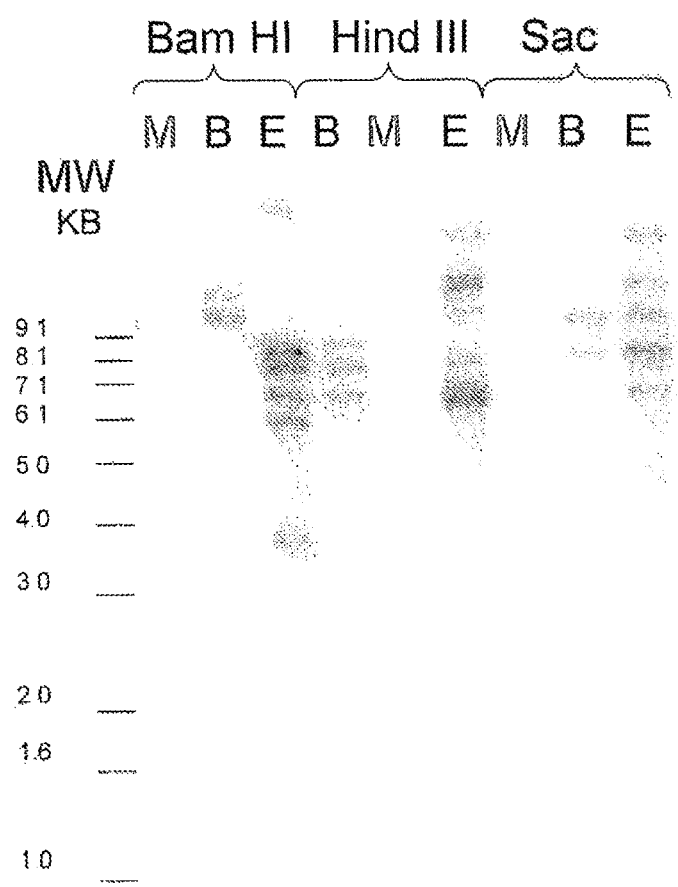
FIG. 9 shows a southern blot showing transformed *T. reesei* strains that had been transformed with multiple copies of the "lipase 3" lipolytic enzyme gene, the lanes are labelled as follows:
M—Untransformed host strain;
B—strain transformed using biolistic transformation;
E—strain transformed using electroporation.
Figure 10:
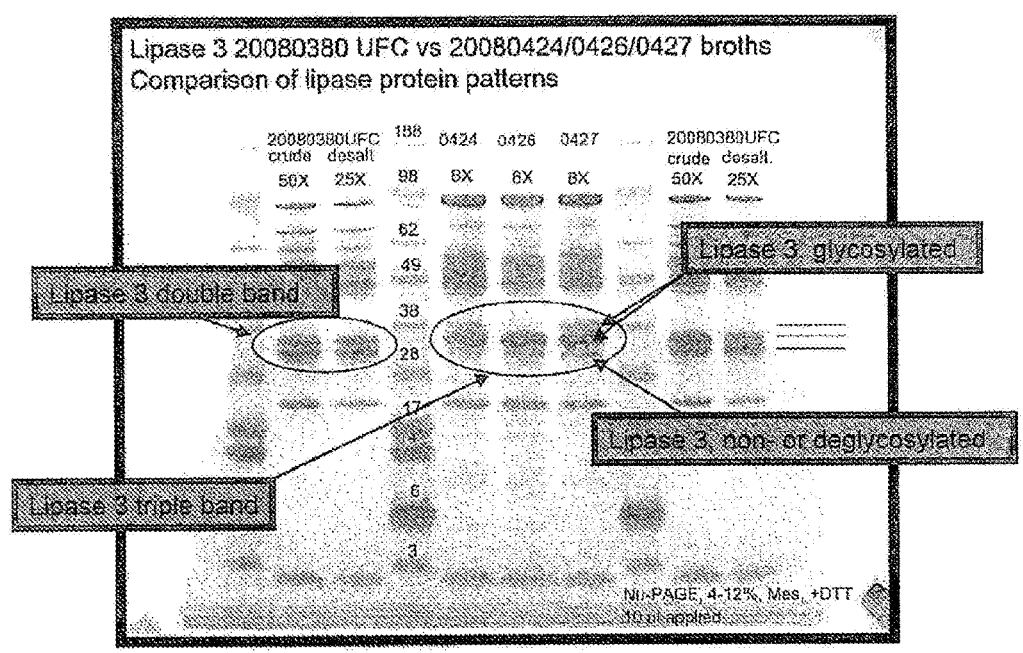
FIG. 10 shows a protein profile by SDS-PAGE used to characterise the lipolytic enzyme ("lipase 3") expressed in *Trichoderma reesei*. Samples from cultures grown in different broths showed lipase 3 protein as double or triple bands.

FIG. 9 shows a southern blot showing transformed *T. reesei* strains that had been transformed with multiple copies of the "lipase 3" lipolytic enzyme gene, the lanes are labelled as follows:

M—Untransformed host strain;
B—strain transformed using biolistic transformation;
E—strain transformed using electroporation;

Example 8

Expressions Studies

Lipase from *Thermomyces lanuginosus* was cloned and expressed in *T. reesei*. Transformants were isolated and the best lipase producer was tested in 14-Liter scale fermentation to investigate whether *Trichoderma reesei* is a suitable host strain for expression of other lipases. The total protein at the end of (200 hours) fermentation was estimated to be in excess of 20 g/L as shown in FIG. 14. SDS-PAGE showed that lipase was the dominant protein produced. Lipase activity measured at the end of fermentation was 30,000 U/mL using DGGR assay. The broth was filtered and concentrated to UFC at high concentration the lipase appeared to precipitate. It was easily brought back into solution by diluting in buffer or salt.

Example 9

Expression Studies

Table 3 provides the results of a series of expression studies.

The present inventors have surprising found that the lipolytic enzyme "Lipase 3" produced in *Trichoderma reesei* is less glycosylated (in particular less N-linked glycosylation) compared with the same enzyme produced in other organisms.

TABLE 3

Comparison with other hosts used to express lipase 3 from *Aspergillus tubingensis*.

| Expression Host | Glycosylation at N32 & N242 sites | Protein Quality |
|---|---|---|
| *Aspergillus tubigensis* 3M | Hyperglycosylation (overglycosylation 10%) (both N32 & N242 sites) | Reduced Activity |
| *Pichia pastoris* GS115 | Hyperglycosylation (both N32 & N242 sites) O-glycans | Activity > activity seen with *A. tubigensis* recombinant lipase strain |
| *Hansenula polymorpha* RB11 | Glycosylation (both N32 & N242 sites) Glycan 1% | Activity > activity seen with *A. tubigensis* recombinant lipase strain |
| *T. reesei* | Majority of N-glycosylation at N32 | Activity is same as native lipase 3 from non-recombinant *Aspergillus* 1M341 strain |

Example 10

The expression host cells suitable for use in the present invention may be a strain of *T. reesei* in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated by deletion or disruption using molecular genetic techniques. This strain (a quad delete strain) is useful as a host for overexpression of genes encoding other *T. reesei* secreted proteins.

Preferably host cells suitable for use in the present invention may be derived from a *Trichoderma reesei* cell of the strain RL-P37 using the methods described in WO 2005/001036 and US28026376 A1.

A *T. reesei* strain suitable for use in the present invention may be derived from the publicly available strain of *T. reesei* RL-P37. *T. reesei* strain RL-P37 may be modified to form *T. reesei* strain 1A52 as described in WO 05/001036. *T. reesei* strain 1A52 may be modified as described in US 20080026376 to form a *T. reesei* cell usable in the present invention.

RL-P37 may be modified to form *T. reesei* strain 1A52 as described below.

The *T. reesei* host strain used may be derived from the publicly available strain RL-P37 which has previously been used to manufacture commercial cellulase preparations by Genencor International, Inc. The derivation and characterisation of this strain has been published previously (Sheir-Neiss, G. and Montenecourt, B. S. (1984) Appl. Microbiol. Biotechnol. 20:46-53; U.S. Pat. No. 4,797,361). It is a cellulase over-producing mutant strain which has been obtained as a result of several mutagenesis steps from the wild-type strain (QM6a).

1) Isolation of a Pyr4 Mutant Strain.

In order to prepare strain RL-P37 for transformation with plasmid DNA it was necessary to isolate a derivative having a null mutation in the pyr4 gene.

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of *T. reesei* strain RL-P37 were spread on the surface of a solidified medium containing 2 mg/ml uridine and 1.2 mg/ml FOA. Spontaneous FOA-resistant colonies appeared within three to four days. FOA-resistant mutants which required uridine for growth were identified. In order to identify those mutants which specifically had a defective pyr4 gene protoplasts were generated and transformed with a plasmid containing a wild-type pyr4 gene (Smith, J. L., Bayliss, F. T. and Ward, M. (1991) Curr. Genet. 19:27-33). Following transformation protoplasts were plated on medium lacking uridine. Subsequent growth of transformed colonies demonstrated complementation of a defective pyr4 gene by the plasmid-borne pyr4 gene. In this way strain GC69 was identified as a pyr4 mutant of strain RL-P37.

2) Construction of a Plasmid Designed to Delete the CBH1 Encoding Gene.

The cbh1 gene, encoding the CBHI protein, was cloned from the genomic DNA of strain RL-P37 by hybridization with an oligonucleotide probe designed on the basis of the published sequence for this gene (Shoemaker, S., Schweickart, V., Ladner, M., Gelfand, D., Kwok, S., Myambo, K. and Innis, M. (1983) Biotechnology 1:691-696). The cbh1 gene resides on a 6.5 kb Pst1 fragment and was inserted into the Pst1 site of pUC4K (Pharmacia Inc., Piscataway, N.J., USA) replacing the kanamycin-resistance gene of this vector. The resulting plasmid, pUC4K::cbh1, was then cut with Hind111 and the larger fragment was isolated and religated to give pUC4K::cbh1ΔH/H. This procedure removed the entire cbh1 coding sequence and approximately 1.2 kb of 5' and 1.5 kb of 3' flanking sequences. Approximately 1 kb of flanking DNA remained from either end of the original Pst1 fragment. The *T. reesei* pyr4 gene was cloned as a 6.5 kb Hind111 fragment of genomic DNA in pUC18 to form pTpyr2 (Smith, J. L., Bayliss, F. T. and Ward, M. (1991) Curr. Genet. 19:27-33). The plasmid pUC4K::cbh1ΔH/H was cut with Hind111 and the ends were dephosphorylated with calf intestinal alkaline phosphatase. This DNA was ligated with the 6.5 kb Hind111 fragment containing the pyr4 gene to give pΔCBH1pyr4.

Digestion of pΔCBH1pyr4 with EcoR1 liberated a larger fragment which consisted of flanking regions of the cbh1 locus at either end with the pyr4 gene replacing the cbh1 coding sequence in the centre. The only DNA on this fragment which was not derived from *T. reesei* was a 21 bp fragment derived from the multiple cloning site of pUC4K.

3) Deletion of the cbh1 Gene of *T. reesei*.

Protoplasts isolated from mycelium of strain GC69 were transformed with EcoR1 digested plasmid pΔCBH1pyr4 using methods outlined by Smith et al., 1991. Stable transformants were obtained and those from which the cbh1 gene had been deleted were identified as described below.

Total DNA was isolated from the transformants, digested with Pst1, subjected to agarose gel electrophoresis and blotted to a membrane filter. The filter was then hybridised with P32 labelled pΔCBH1pyr4 and the pattern of hybridisation observed by autoradiography. This probe hybridised with the native cbh1 and pyr4 genes in an untransformed strain. In one transformant (strain P37PΔCBHI) a pattern of hybridisation was observed which would be predicted if a double cross-over integration event had occurred. That is, the cbh1 gene had been deleted by integration of a single copy of the larger EcoR1 fragment obtained from pΔCBH1pyr4 at the cbh1 locus of strain RL-P37.

Southern analysis was also performed as above except that the probe used was radiolabelled pintCBHI. This plasmid consists of a pUC vector containing a 2 kb Bgl11 fragment from the cbh1 locus within the region that was deleted in pUC4K::cbh1ΔH/H. This plasmid hybridised to the cbh1 locus of strain GC69 but did not hybridise to DNA from strain P37PΔCBHI. This confirms that the cbh1 gene had been deleted and that the pUC DNA fragment from pΔCBH1pyr4 had not been incorporated by the deleted strain.

Analysis of secreted proteins by separation on isoelectric focusing gels showed that the CBH1 protein was not produced by strain P37PΔCBHI.

4) Generation of a Pyr4 Null Mutant of P37PΔCBHI.

Spores of the transformant (P37PΔCBHI) which was deleted for the cbh1 gene were spread onto medium containing FOA. A pyr4 deficient derivative of this transformant was subsequently obtained using the methods described in section above. This pyr4 deficient strain was designated P37PΔCBHIPyr⁻26. Southern analysis has shown that a spontaneous deletion had occurred when strain P37PΔCBHIPyr⁻26 was selected. This deletion completely removed the pyr4 gene which had integrated at the cbh1 locus in strain P37PΔCBHI, as well as flanking DNA from the cbh1 locus beyond the extent of the 6.5 kb Pst1 fragment of genomic DNA which was originally cloned.

5) Construction of a Vector Designed to Delete the cbh2 Gene.

The cbh2 gene of *T. reesei*, encoding the CBH11 protein, has been cloned as a 4.1 kb EcoR1 fragment of genomic DNA (Chen et al., 1987, Biotechnology 5:274-278). This 4.1 kb fragment was inserted between the EcoR1 sites of pUC4XL. The latter plasmid is a pUC derivative (constructed by R. M. Berka, Genencor International Inc.) which contains a multiple cloning site with a symetrical pattern of restriction endonuclease sites arranged in the order shown here. EcoRI, BamHI, Sac1, Sma1, Hind111, Xhol, Bgl11, Cla1, Bgl11, Xhol, Hind11 I, Sma1, Sac1, BamHI, EcoRI. The plasmid, pPΔCBH11 was constructed in which a 1.7 kb central region of this cbh2 clone, between a Hind111 site (at 74 bp 3' of the CBH11 translation initiation site) and a ClaI site (at 265 bp 3' of the last codon of CBHII), has been removed and replaced by a 1.6 kb Hind111-Cla1 DNA fragment containing the *T. reesei* pyr4 gene obtained as follows. The *T. reesei* pyr4 gene was excised from pTpyr2 on a 1.6 kb Nhe1-Sph1 fragment and inserted between the Sph1 and Xba1 sites of pUC219 (derived from pUC119 by expanding the multiple cloning site to include restriction sites for Bgl11, Cla1 and Xhol; Wilson et al., 1989, Gene 77:69 78) to create p219M (Smith et al., 1991, Curr Genet. 19:27-33). The pyr4 gene could then be removed as a Hind111-Cla1 fragment having seven by of DNA at one end and six by of DNA at the other end derived from the pUC219 multiple cloning site and inserted into the Hind111 and Cla1 sites of the cbh2 gene to form the plasmid pPΔCBHII.

Digestion of this plasmid with EcoR1 liberated a fragment having 0.7 kb of flanking DNA from the cbh2 locus at one end, 1.7 kb of flanking DNA from the cbh2 locus at the other end and the *T. reesei* pyr4 gene in the middle. The only DNA in this fragment which was not derived from *T. reesei* was the 6 bp and 7 bp fragments of the pUC219 multiple cloning site at either end of the pyr4 gene.

6) Deletion of cbh2 Gene from Strain P37PΔCBHIPyr⁻26

Protoplasts of strain P37PΔCBHIPyr⁻26 were generated and transformed with EcoR1 digested pPΔCBHII according to the methods outlined in 3 above. Stable transformants were cultured in shake flasks and the protein in the culture supernatants was examined by isoelectric focussing. One transformant (designated P37PΔΔCBH67) was identified which did not produce any CBH11 (nor CBHI) protein.

was extracted from strain P37PΔΔCBH67, digested with EcoR1 and Asp718, and subjected to agarose gel electrophoresis. The DNA from this gel was blotted to a membrane filter and hybridized with 32P labelled pPΔCBHII. The 4.1 kb EcoR1 fragment containing the wildtype cbh2 gene was observed in the DNA from an untransformed control strain. In contrast, in strain P37PΔΔCBH67 the single 4.1 kb band was eliminated and replaced by two bands of approximately 0.9 and 3.1 kb. This is the expected pattern if a single copy of the larger EcoR1 fragment from pPΔCBH11 had integrated precisely at the cbh2 locus and deleted the cbh2 gene.

The same DNA samples were also digested with EcoR1 and Southern analysis was performed as above. In this example the probe was 32P labelled pintCBHII. This plasmid contains a portion of the cbh2 gene coding sequence from within that segment of cbh2 DNA which was deleted in plasmid pPΔCBHII. No hybridization was seen with DNA from strain P37PΔCBH67 confirming that the cbh2 gene was deleted and that the pUC plasmid fragment of pPΔCBH1I had not been incorporated by this strain.

7) Selection of a Pyr4 Null Mutant of Strain P37PΔΔCBH67.

Spores of the transformant (P37PΔΔCBH67) which was deleted for both the cbh1 and cbh2 genes were spread onto medium containing FOA. A pyr4 deficient derivative of this transfomant was subsequently obtained using the methods described in section 1 above. This pyr4 deficient strain was designated P37PΔΔCBH67Pyr⁻1. Southern analysis has shown that a spontaneous deletion had occurred when strain P37PΔΔCBH67Pyr⁻1 was selected. This deletion completely removed the pyr4 gene which had integrated at the cbh2 locus in strain P37PΔCBH67, as well as flanking DNA from the cbh2 locus beyond the extent of the 4.1 kb EcoR1 fragment of genomic DNA which was originally cloned. The short (6 bp and 7 bp) fragments of DNA derived from the pUC219 multiple cloning site which were present at either end of the pyr4 gene would also have been removed from the genome by this deletion.

8) Construction of a Plasmid Designed to Disrupt the egl2 Gene.

The egl2 gene, encoding EGl1 (previously referred to as EGl11 by some), has been cloned from *T. reesei* and the DNA sequence published (Salohemo et al., 1988, Gene 63:11-21). We have obtained the gene from strain RL-P37 as an approximately 4 kb Pst1-Xhol fragment of genomic DNA inserted between the Pst1 and Xhol sites of pUC219. The *T. reesei* pyr4 gene, present on a 2.7 kb SalI fragment of genomic DNA obtained from pTpyr2, was inserted into a Sal1 site within the EGl1 coding sequence to create plasmid pEGII::P-1. This resulted in disruption of the EGl1 coding sequence but without deletion of any sequences. The plasmid, pEGII::P-1, can be digested with Hind111 and BamH1 to yield a linear fragment of DNA derived exclusively from *T. reesei* except for 5 bp on one end and 16 bp on the other end both of which are derived from the multiple cloning site of pUC219.

9) Disruption of the egl2 Gene of Strain P37PΔCBH67Pyr⁻1.

Strain P37PΔΔCBH67Pyr⁻1 was transformed with pEGII::P-1 which had been previously digested with Hind111 and BamH1 and stable transformants were selected. Total DNA was isolated from transformants and Southern analysis used to identify strains in which the fragment of plasmid DNA containing the pyr4 and egl2 genes had integrated at the egl2 locus and consequently disrupted the EGl1 coding sequence. Southern analysis was performed using as a probe an approximately 4 kb Pst1 fragment of *T. reesei* DNA containing the egl2 gene. When DNA isolated from strain P37PΔΔ67P⁻1 was digested with Pst1 for Southern analysis the egl2 locus was subsequently visualised as a single 4 kb band on the autoradiograph. However, for a transformant disrupted for the egl2 gene this band was lost and was replaced by two new bands as expected. When the DNA was digested with Bgl11 or EcoRV the size of the band corresponding to the egl2 gene increased in size by approximately 2.7 kb (the size of the inserted pyr4 fragment) between the untransformed P37PΔΔ67P⁻1 strain and the transformant disrupted for egl2. This latter transformant, now deleted for the cbh1, cbh2, and egl2 genes, was designated as strain B31. Further Southern analysis confirmed that the pUC DNA fragment of pEGII::P-1 was not incorporated in this strain.

10) Selection of a pyr4 Null Mutant of Strain B31.

Spores of the transformant (B31) which was deleted for the cbh1, cbh2 and egl2 genes were spread onto medium containing FOA. A pyr4 deficient derivative of this transformant was subsequently obtained using the methods described in section 1 above. This pyr4 deficient strain was designated B31P6. Southern analysis has shown that a spontaneous deletion had occurred when strain B31P6 was selected. This deletion removed the majority of the pyr4 gene which had integrated at the egl2 locus in strain B31, but did not extend into the flanking DNA of the egl2 locus.

11) Construction of a Plasmid Designed to Delete the egl1 Gene.

The egl1 gene of *T. reesei* has been cloned and the DNA sequence of the gene has been published (Penttila et al., 1986, Gene 45; 253-263; van Arsdell et al., 1987, Bioltechnology 5:60-64). We have obtained this gene from *T. reesei* strain RL-P37 as a 4.2 kb Hind111 fragment of genomic DNA inserted at the Hind111 site of pUC100 (a derivative of pUC18 with an oligonucleotide inserted into the multiple cloning site adding restriction sites for Bgl11, Cla1 and Xhol) to give pUCEGI. An approximately 1 kb EcoRV fragment extending from a position close to the middle of the EGI coding sequence to a position beyond the 3' end of the coding sequence was removed and replaced by a 3.5 kb Sca1 fragment of *T. reesei* DNA containing the pyr4 gene obtained from pTpyr2. The resulting plasmid was called pPΔEGI.

The plasmid, pPΔEG1 could be digested with Hind111 to release a DNA fragment comprising only *T. reesei* genomic DNA having a segment of the egl1 gene at either end and the pyr4 gene, replacing part of the EGI coding sequence, in the centre.

12) Deletion of the eal1 Gene in Strain B31P6.

Two forms of pPΔEG1 were constructed which differed only in the orientation of the pyr4 gene with respect to the egl1 flanking regions. Strain B31P6 was transformed with a mixture of both forms of the plasmid after they had been digested with Hind111. Total DNA was extracted from stable transformants, digested with Hind111 and subjected to Southern analysis. The probe used was radio labelled pUCEGI. Hybridisation was observed to a 4.2 kb fragment of DNA from strain B31P6 representing the undeleted egl1 gene. A transformant (strain 1A52) was identified in which this 4.2 kb was no longer present but had been replaced by a fragment of approximately 6.8 kb. This is the pattern expected if the larger Hind111 fragment from pPΔEGI had integrated precisely as predicted at the egl1 locus leading to deletion of part of the EGI coding sequence and insertion of pyr4 at this position. Using a pUC plasmid as a probe for Southern analysis it was confirmed that the pUC DNA fragment of pPΔEGI had not been incorporated in strain 1A52.

*T. reesei* strain 1A52 may be modified to form a *T. reesei* cell usable in the present invention.

Example 11

Assay Protocols

Assay for Triacylglycerol Hydrolysing Activity (Classified as E.C. 3.1.1.3)
LIPU/LUSol assays for Triacylglycerol hydrolysing activity Determination of lipase activity by LIPU is carried out by enzymation of an emulsion of tributyrylglycerol. Enzymatic hydrolysis of lipids liberates free fatty acids. By continuous titration of the liberated free fatty acid, the lipase activity is determined from the consumption of base. 1 LIPU (lipase unit) (also called 1 unit herein) is defined as the amount of enzyme, which releases 1 μmol free fatty acid per minute at the given assay conditions.

Enzyme samples were dissolved in demineralised water. The titrant was 0.05 M NaOH. The substrate was a homogenised emulsion of 5% (v/v) tributyrineglycerol (Merck, item no. 1.01958), 0.10% (w/v) gum arabic (Sigma, item no. G9752), 7.5% (w/v) glycerol (Merck, item no. 1.04092), 51 mM NaCl (p.a. Merck, item no. 1.06404), 0.50 mM KH2PO4 (p.a. Merck, item no. 1.04873). Reaction pH was 5.5 and reaction temperature was 30° C. 2.00 mL sample was added to 25.0 mL substrate acclimatized to the reaction temperature. Activity was calculated from the slope of a linear titration curve with consumption of titrant plotted against reaction time.

Substrates used are Tributyrin (Lipu) and Sunflower oil (LUSol).

DGGR Assay for Triacylglycerol Hydrolysing Activity

This assay was used to measure *Thermomyces lanuginosus* lipase expressed in *Trichoderma*.

The substrates and buffers used in this assay were the following:

3.32 mM 1,2-Di-O-lauryl-rac-glycero-3-(glutaric acid 6-methylresorufin ester) dissolved in DMSO (substrate, 2.5 mg/mL);

A stock solution consisting of 50 mg substrate added to 20 mL DMSO is sonicated, aliquoted and stored at −80 deg C. until use. Buffer used is 0.5 M HEPES pH 8+60 gpg 3:1 Ca:Mg Water hardness (see CAM300) and 4% Gum Arabic. Lipase enzyme stock (1 mg/L) is used as standard.

For the assay, A 50 mL assay buffer is prepared by adding 5 mL HEPES+Hardness and 25 mL 4% Gum Arabic to 10 mL water. The assay buffer is incubated to desired assay temperature (typically 25 deg C.). 10 uL of enzyme samples are added into 96-well plate at assay temperature. 1-10 ppm of active enzyme in sample recommended.

For best results match unknown concentration to +/−two-fold activity of standard.

The background rate (no enzyme, i.e. assay buffer) is determined.

10 mL of 3.32 mM DGGR substrate in DMSO is added to assay buffer and mixed well using a vortex. 200 uL substrate in assay buffer is added immediately to enzyme samples in microplate from a reagent reservoir using a multi-channel pipet. The microtiter plate is mixed well and immediately transfer ed to plate reader. OD at 580 nm for up to 10 min is measured at desired assay temperature (typically 25 deg C.). Calculation of the enzyme activity is done by subtracting the background rate from unknown and standard to obtain difference rates. Determine the ratio of the difference rates for unknown to standard and multiply by the standard concentration. All dilutions are included in the calculation:

unknown concentration=(unknown Rate*standard concentration)/standard rate.

Determination of Triacylglyceride Lipase Activity: Assay Based on Triglyceride (Tributyrin) as Substrate (LIPU):

Lipase activity based on tributyrin is measured according to Food Chemical Codex, Forth Edition, National Academy Press, 1996, p 803, with the modifications that the sample is dissolved in deionized water instead of glycine buffer, and the pH stat set point is 5.5 instead of 7.

1 LIPU is defined as the quantity of enzyme which can liberate 1 mol butyric acid per minute under assay conditions.

Assay for Phospholipase Activity
  phospholipase A1 activity (E.C. 3.1.1.32)
  phospholipase A2 activity (E.C. 3.1.1.4)
  phospholipase B activity (E.C. 3.1.1.5)
Substrate 1.75% L—Plant Phosphatidylcholin 95% (441601, Avanti Polar Lipids), 6.3% Triton X-100 (#T9284, Sigma) and 5 mM CaCl2 dissolved in 50 mM HEPES buffer pH 7.0.

Assay Procedure

Samples, calibration and control were diluted in 10 mM HEPES pH 7.0, 0.1% Triton X-100 (#T9284, Sigma). Analysis was carried out using a Konelab Autoanalyzer (Thermo, Finland). The assay was run at 30 C. 34 µL substrate was thermostated for 180 seconds, before 4 µL sample was added. Enzymation lasted for 600 s. Amount of free fatty acid liberated during enzymation was measured using the NEFA C kit (999-75406, WAKO, Germany). 56 µL NEFA A was added and the mixture was incubated for 300 s. Afterwards 113 µL NEFA B was added and the mixture was incubated for 300 s. Afterwards 113 µl NEFAB was added and the mixture was incubated for 300 s. OD 520 nm was then measured. Enzyme activity LATU (µmol FFA/minmL) was calculated based on a standard enzyme preparation.

Assay for Glycolipase (Galactolipase) Activity.
Substrate 1.75% Didalactosyldiglyceride (DGDG, Purified from wheat lipids), 6.3% Triton X-100 (#T9284, Sigma) and 5 mM CaCl2 dissolved in 50 mM HEPES buffer pH 7.0.

Assay Procedure

Samples, calibration and control were diluted in 10 mM HEPES pH 7.0, 0.1% Triton X-100 (#T9284, Sigma). Analysis was carried out using a Konelab Autoanalyzer (Thermo, Finland). The assay was run at 30 C. 34 µL substrate was thermostated for 180 seconds, before 4 µL sample was added. Enzymation lasted for 600 s. Amount of free fatty acid liberated during enzymation was measured using the NEFA C kit (999-75406, WAKO, Germany). 56 µL NEFA A was added and the mixture was incubated for 300 s. Afterwards 113 µL NEFA B was added and the mixture was incubated for 300 s. Afterwards 113 µl NEFAB was added and the mixture was incubated for 300 s. OD 520 nm was then measured. Enzyme activity GLU-K (µmol FFA/minmL) was calculated based on a standard enzyme preparation.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What the invention claimed is:

1. A method of producing a lipolytic enzyme comprising the steps of:
providing a transformed or transfected *Trichoderma reesei* cell comprising one or more of:
(i) at least one heterologous nucleotide sequence encoding a lipolytic enzyme comprising an amino acid sequence shown as SEQ ID NO: 1 or SEQ ID NO: 2 or an amino acid sequence which has at least 90% sequence identity to SEQ ID NO: 1 or 2,
(ii) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which has at least 90% sequence identity to SEQ ID NO: 3 or SEQ ID NO: 4, or
(iii) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 90% sequence identity to SEQ ID NO: 3 or SEQ ID NO: 4 or the complement of any thereof under high stringency conditions of 0.1×SSC at 65° C., where 1×SSC comprises 0.15 M sodium chloride and 0.015 M sodium citrate at pH 7.0;
culturing the cell under conditions to allow for expression of said heterologous nucleotide sequence(s) encoding said lipolytic enzyme; and
raising the pH at the end of fermentation that occurs during the culturing of the cell to a pH above the pH of the culture conditions.

2. The method of claim 1, wherein the heterologous nucleotide sequence further comprises a promoter sequence, which promoter sequence is a cellobiohydrolase promoter sequence.

3. The method of claim 1, wherein the lipolytic enzyme is produced in an amount of at least 20 g/liter of culture supernatant.

4. The method of claim 1, wherein said method comprises one or more of concentrating, isolating, or recovering the lipolytic enzyme.

5. The method of claim 1, wherein the *Trichoderma reesei* cell is prepared by transforming or transfecting a *Trichoderma reesei* cell with the nucleotide sequence.

6. The method of claim 1, wherein the *Trichoderma reesei* cell is provided by transforming it with or is transformed with the nucleotide sequence using biolistic transformation.

7. A *Trichoderma reesei* cell comprising:
a sequence comprising one or more of:
(i) at least one heterologous nucleotide sequence encoding a lipolytic enzyme protein having at least 90% sequence identity to SEQ ID NO: 1 or 2;
(ii) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which is at least 90% sequence identity to SEQ ID NO: 3 or SEQ ID NO: 4; or
(iii) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 90% sequence identity to SEQ ID NO: 3 or SEQ ID NO: 4 or the complement of any thereof under high stringency conditions of 0.1×SSC at 65° C., where 1×SSC comprises 0.15 M sodium chloride and 0.015 M sodium citrate at pH 7.0; and
the lipolytic enzyme encoded by the heterologous nucleotide sequence with improved glycosylation pattern and high expression yield compared to lipolytic enzymes produced by different hosts.

8. The *Trichoderma reesei* cell of claim 7, wherein the cell comprises at least two heterologous nucleotide sequences encoding said lipolytic enzyme.

9. A method of producing an active lipolytic enzyme by a *Trichoderma reesei* cell to use in foodstuff, the method comprising:

transforming or transfecting the *Trichoderma reesei* cell comprising one or more of:
(i) at least one heterologous nucleotide sequence encoding a lipolytic enzyme comprising an amino acid sequence shown as SEQ ID NO: 1 or SEQ ID NO: 2 or an amino acid sequence which has at least 90% sequence identity to SEQ ID NO:1 or 2;
(ii) at least one heterologous nucleotide sequence encoding a lipolytic enzyme wherein the nucleotide sequence comprises the nucleotide sequence shown as SEQ ID NO: 3 or SEQ ID NO: 4 or a nucleotide sequence which is at least 90% sequence identity to SEQ ID NO: 3 or SEQ ID NO: 4; or
(iii) at least one heterologous nucleotide sequence encoding a lipolytic enzyme wherein the nucleotide sequence comprises a nucleotide sequence which hybridizes to SEQ ID NO: 3 or SEQ ID NO: 4 or a nucleotide sequence which is at least 90% sequence identity to SEQ ID NO: 3 or SEQ ID NO: 4 or the complement of any thereof under high stringency conditions of 0.1×SSC at 65° C., where 1×SSC comprises 0.15 M sodium chloride and 0.015 M sodium citrate at pH 7.0; for improving one or more of the following: expression of the lipolytic enzyme, glycosylation of the lipolytic enzyme, enzyme activity, or yield;
culturing the cell under conditions to allow for expression of said heterologous nucleotide sequence(s) encoding said lipolytic enzyme; and
raising the pH at the end of fermentation that occurs during the culturing of the cell to a pH above the pH of the culture conditions.

10. The method of claim 9, wherein after expression of the nucleotide sequence the *Trichoderma reesei* cell is removed from the medium into which the enzyme has been secreted.

11. The method of claim 9, wherein after expression of the nucleotide sequence the *Trichoderma reesei* cell is removed from the medium into which the enzyme has been secreted; and then the cell free medium is concentrated.

12. The method of claim 9, wherein the pH of the medium into which the enzyme is secreted is raised after a period of time to yield sufficient levels of the secreted
enzyme and prior to the isolation and/or purification and/or concentration of the enzyme.

13. The method of claim 9, wherein the following steps are carried out to the medium into which the enzyme of the present invention has been secreted following culturing of the cell: adjusting the pH of the medium, diluting the medium with water; separating the cell(s) from the medium; concentrating the medium wherein said medium is cell-free; and optionally granulating said medium wherein said medium is cell-free.

14. The method of claim 9, wherein the enzyme is used in a method to prepare a food or foodstuff intended for human consumption said method comprising admixing said enzyme with a suitable food or foodstuff ingredient.

15. The method of claim 14, wherein said enzyme is in the medium into which the enzyme of the present invention has been secreted following culturing of the cell.

16. The method of claim 15, wherein said medium is cell-free.

17. The method of claim 16, wherein said medium is concentrated.

18. The method of claim 17, wherein said medium is granulated.

* * * * *